United States Patent
Jung et al.

(10) Patent No.: US 12,006,498 B2
(45) Date of Patent: Jun. 11, 2024

(54) COMPOSITION FOR REGULATING EXPRESSION OF PROX1 OR EXPRESSION OF TELOMERASE REVERSE TRANSCRIPTASE COMPRISING ACTIVITY REGULATOR OR METHOD FOR SCREENING TELOMERASE REVERSE TRANSCRIPTASE REGULATOR

(71) Applicants: KOREA INSTITUTE OF SCIENCE AND TECHNOLOGY, Seoul (KR); INDUSTRY-ACADEMIC COOPERATION FOUNDATION, YONSEI UNIVERSITY, Seoul (KR)

(72) Inventors: Sang Hoon Jung, Gangneung-si (KR); Young-Joo Kim, Gangneung-si (KR); Dae-geun Song, Gangneung-si (KR); Young Nyun Park, Seoul (KR); Jeong Eun Yoo, Incheon (KR); Hyung Jin Rhee, Seoul (KR); Youngsic Jeon, Seoul (KR)

(73) Assignees: KOREA INSTITUTE OF SCIENCE AND TECHNOLOGY, Seoul (KR); INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 0 days.

(21) Appl. No.: 16/761,151

(22) PCT Filed: Oct. 19, 2018

(86) PCT No.: PCT/KR2018/012383
§ 371 (c)(1),
(2) Date: Jun. 2, 2020

(87) PCT Pub. No.: WO2019/088528
PCT Pub. Date: May 9, 2019

(65) Prior Publication Data
US 2023/0250424 A1    Aug. 10, 2023

(30) Foreign Application Priority Data

Nov. 3, 2017    (KR) .................. 10-2017-0146274

(51) Int. Cl.
  *C12N 15/113*    (2010.01)
  *A61P 1/16*    (2006.01)
  *A61P 35/00*    (2006.01)

(52) U.S. Cl.
  CPC .............. *C12N 15/113* (2013.01); *A61P 1/16* (2018.01); *A61P 35/00* (2018.01);
  (Continued)

(58) Field of Classification Search
  CPC .............. C12N 15/113; C12N 2310/14; C12N 2310/141; C12N 2310/531; A61K 48/00; A61P 1/16
  See application file for complete search history.

(56) References Cited

U.S. PATENT DOCUMENTS

2018/0362986 A1    12/2018 Lee et al.

FOREIGN PATENT DOCUMENTS

KR    10-2009-0052670 A    5/2009
KR    10-1600374 B1    3/2016
(Continued)

OTHER PUBLICATIONS

Extended European Search Report for European Application No. 18874248.0, dated May 27, 2021.
(Continued)

*Primary Examiner* — Terra C Gibbs
(74) *Attorney, Agent, or Firm* — Birch, Stewart, Kolasch & Birch, LLP

(57) ABSTRACT

In the present specification, on the basis of the correlation between prospero homeobox protein 1 (PROX1) and telomerase reverse transcriptase (TERT), a composition for
(Continued)

regulating expression of TERT, a method for screening a TERT expression regulator, a composition for diagnosing a TERT expression status, a diagnostic kit, a method for providing information for diagnosis, or a method for providing information for cancer diagnosis are disclosed. Specifically, in one aspect, the PROX1 of the present disclosure may bind to a TERT promoter, in particular a mutant TERT promoter in which base substitution occurs at the −124 or −146 bp position to regulate the expression of TERT, and the expression of TERT in non-hepatitis B virus-associated liver cancer can be inhibited specifically among liver cancers.

7 Claims, 17 Drawing Sheets

Specification includes a Sequence Listing.

(52) U.S. Cl.
CPC ...... *C12N 2310/11* (2013.01); *C12N 2310/12* (2013.01); *C12N 2310/127* (2013.01); *C12N 2310/14* (2013.01); *C12N 2310/141* (2013.01); *C12N 2310/3181* (2013.01); *C12N 2310/531* (2013.01)

(56) References Cited

FOREIGN PATENT DOCUMENTS

| KR | 10-2017-0042490 A | 4/2017 |
| WO | WO 2005/014854 A1 | 2/2005 |
| WO | WO 2008/149353 A2 | 12/2008 |

OTHER PUBLICATIONS

Baxter et al., "Regulation of the lymphatic endothelial cell cycle by the PROX1 homeodomain protein." Biochimica et Biophysica Acta (2011), vol. 1813, pp. 201-212.

Chang et al., "The homeobox transcription factor Prox1 inhibits proliferation of hepatocellular carcinoma cells by inducing p53-dependent senescence-like phenotype," Cancer Biology & Therapy (2013), vol. 14, No. 3, pp. 222-229.

Liu et al., "Prospero-Related Homeobox 1 Drives Angiogensis of Hepatocellular Carcinoma Through Selectively Activaing Interleukin-8 Expression," Hepatology (2017), vol. 66, No. 6, pp. 1894-1909.

Liu et al., "PROX1 Promotes Hepatocellular Carcinoma Metastasis by Way of Up-Regulating Hypoxia-Inducible Factor 1α Expression and Protein Stability," Hepatology (2013), vol. 58, pp. 692-705.

Liu et al., "PROX1 promotes hepatocellular carcinoma proliferation and sorafenib resistance by enhanding β-catenin expression and nuclear translocation," Oncogene (2015), vol. 34, pp. 5524-5535.

[FIG. 1A]
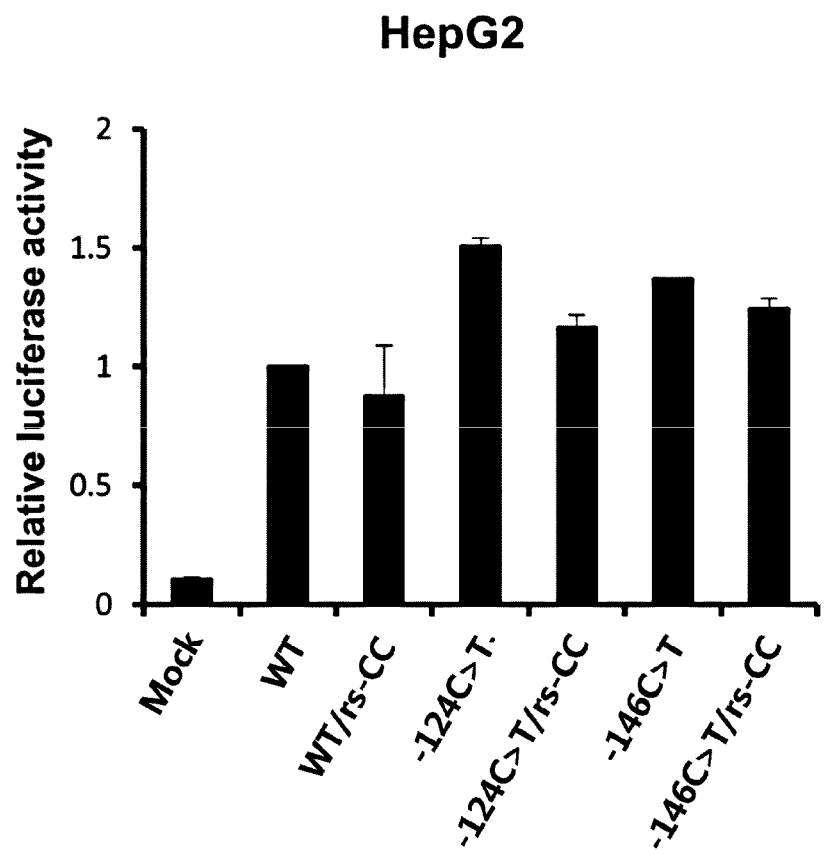

[FIG. 1B]
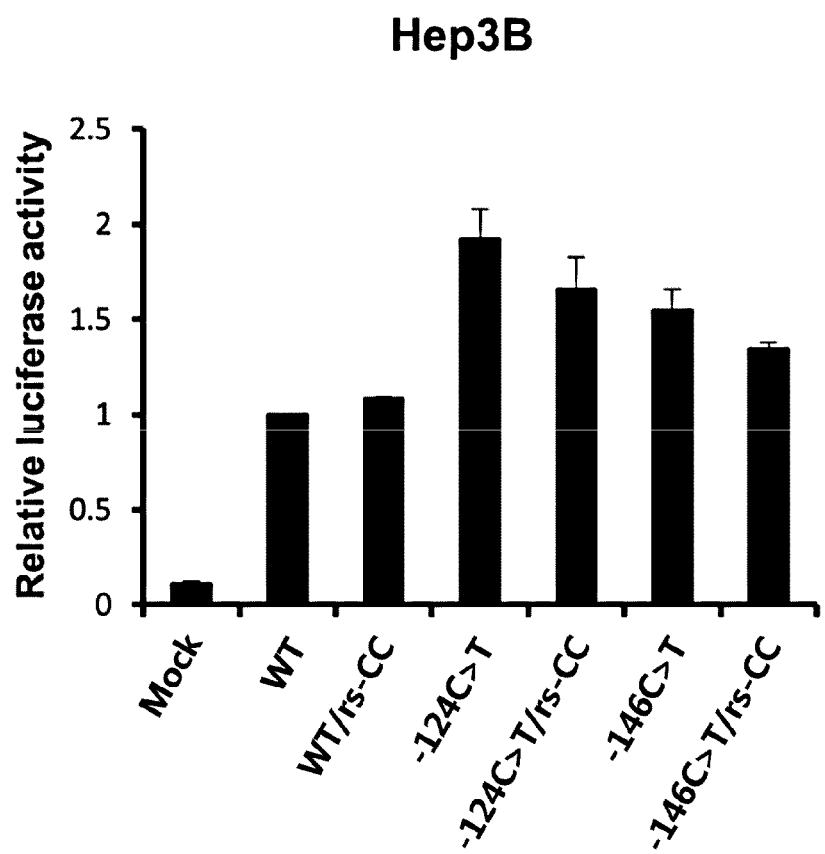

[FIG. 1C]
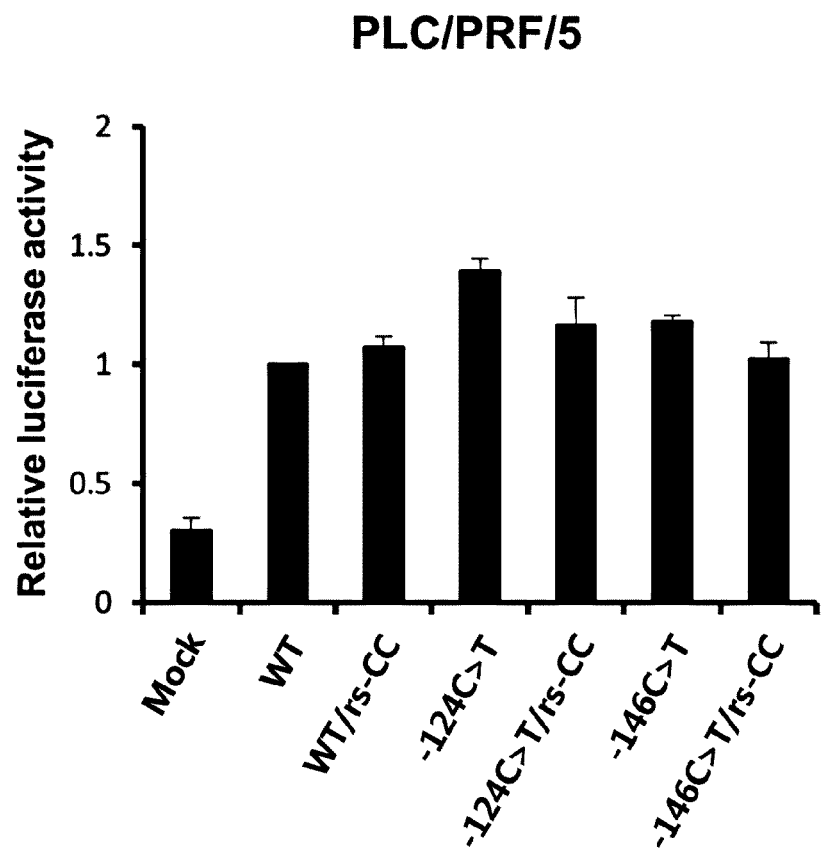

[FIG. 2A]

| Identified Protein Name | $R_{sc}$ | |
|---|---|---|
| | -124C<T | -146C<T |
| Prospero homeobox protein 1 | 3.9 | 4.3 |
| cDNA FLJ76127, highly similar to Homo sapiens replication factor C (activator 1) 5 | 3.5 | 4.3 |
| Nuclease-sensitive element-binding protein 1 | 2.3 | 3.5 |
| Double-strand-break repair protein rad21 homolog | 2.2 | 3.4 |
| Nucleoporin NUP188 homolog | 2.2 | 2.9 |
| Titin, isoform CRA_a | 2.2 | 2.1 |
| SMARCA1 protein | 1.8 | 3.0 |

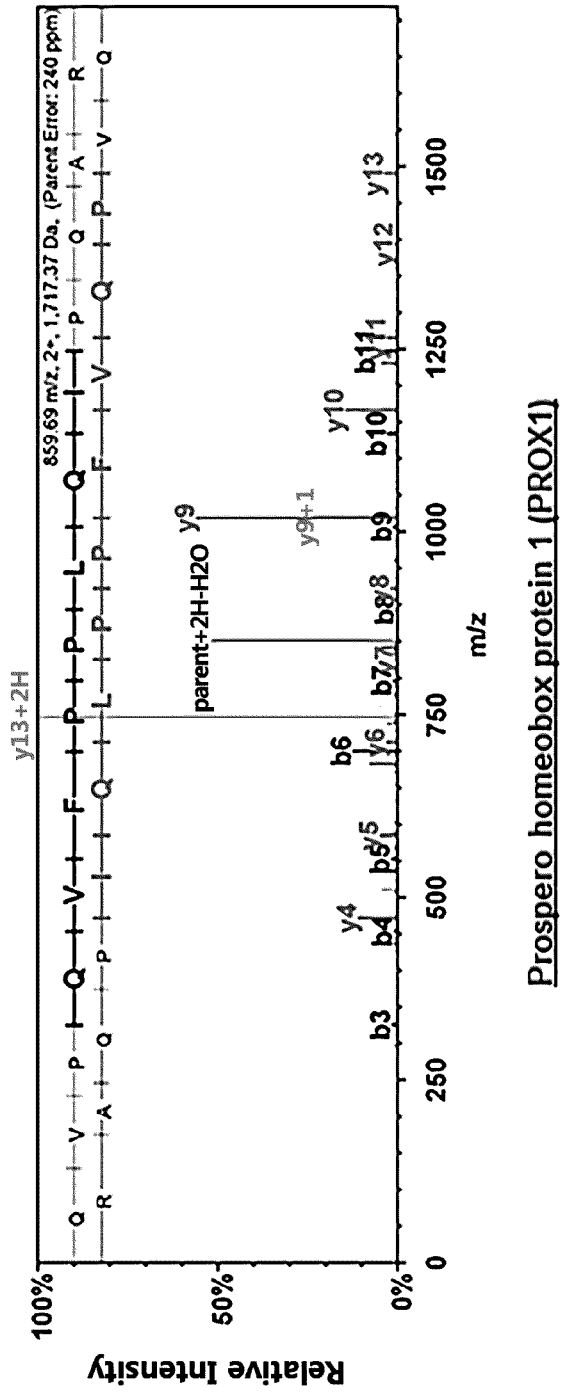
[FIG. 2B]

[FIG. 3]
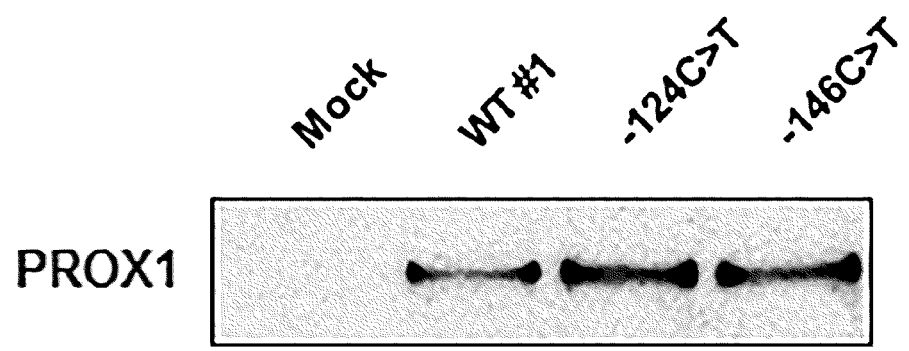

[FIG. 4]
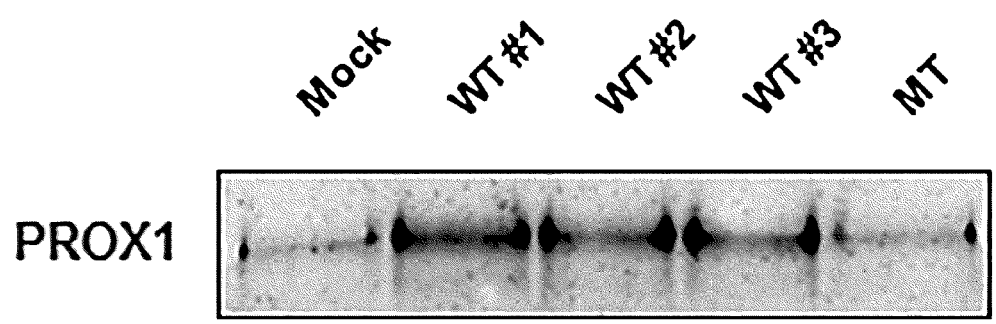
[FIG. 5]
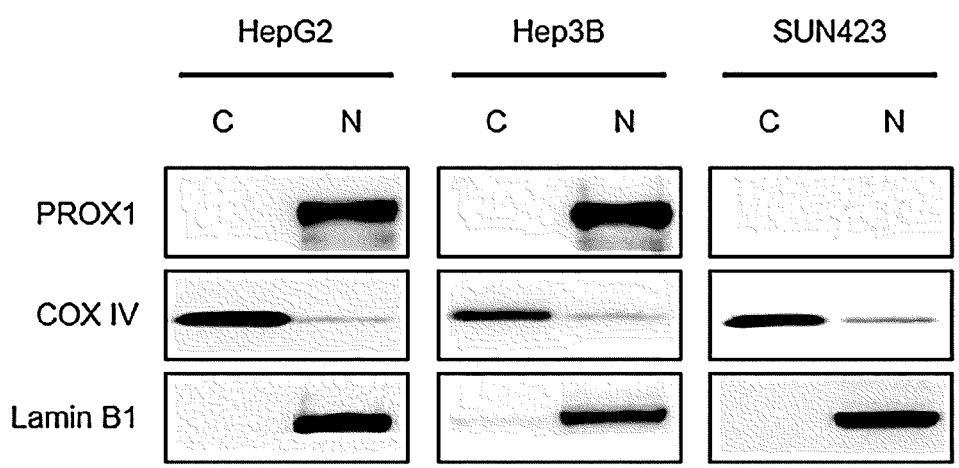

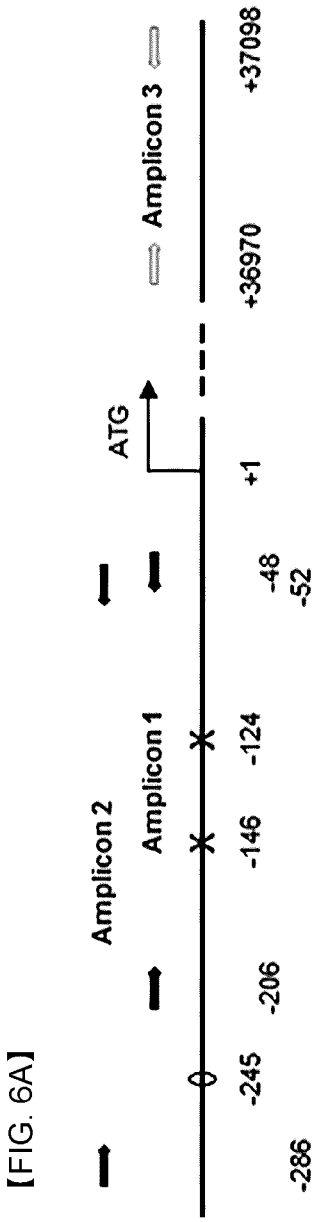
[FIG. 6A]

[FIG. 6B]
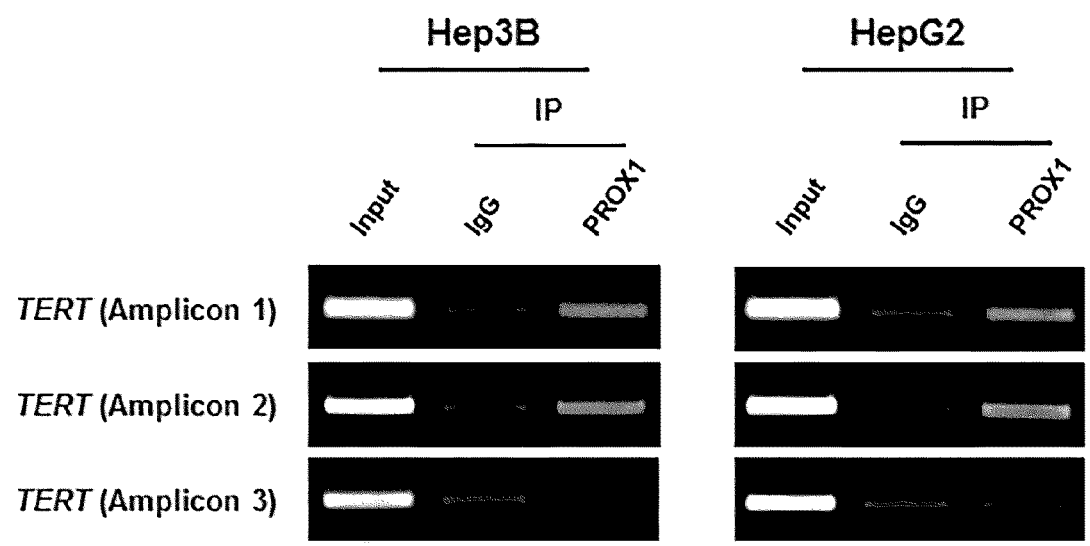

[FIG. 7A]
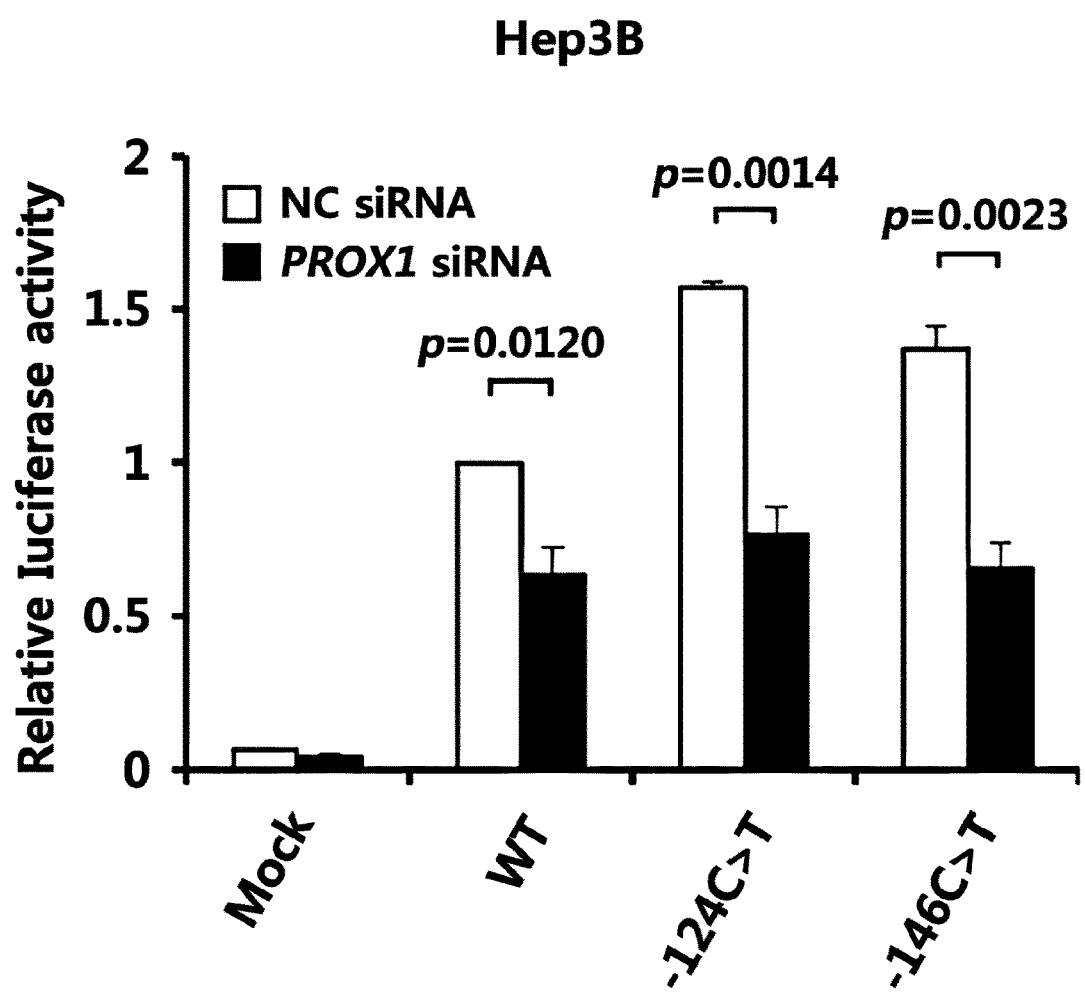

[FIG. 7B]
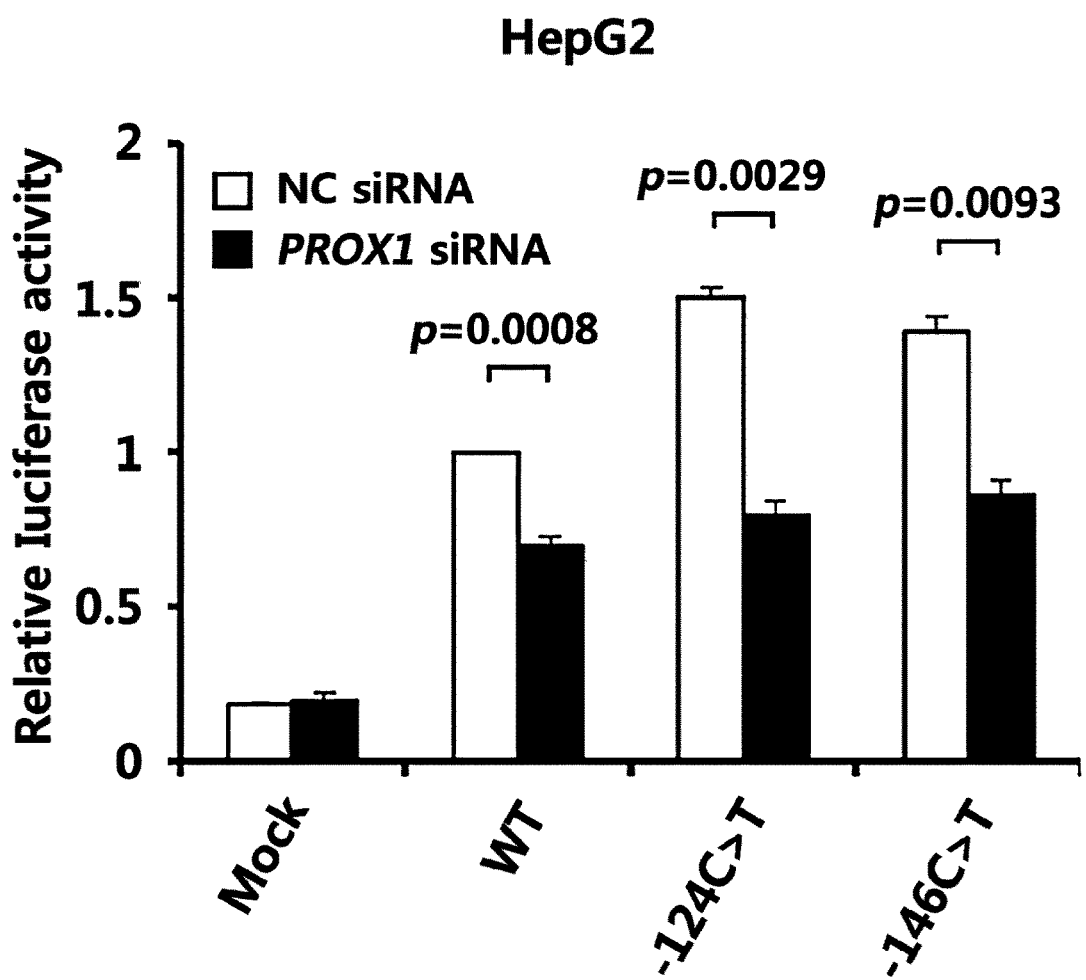

[FIG. 8]
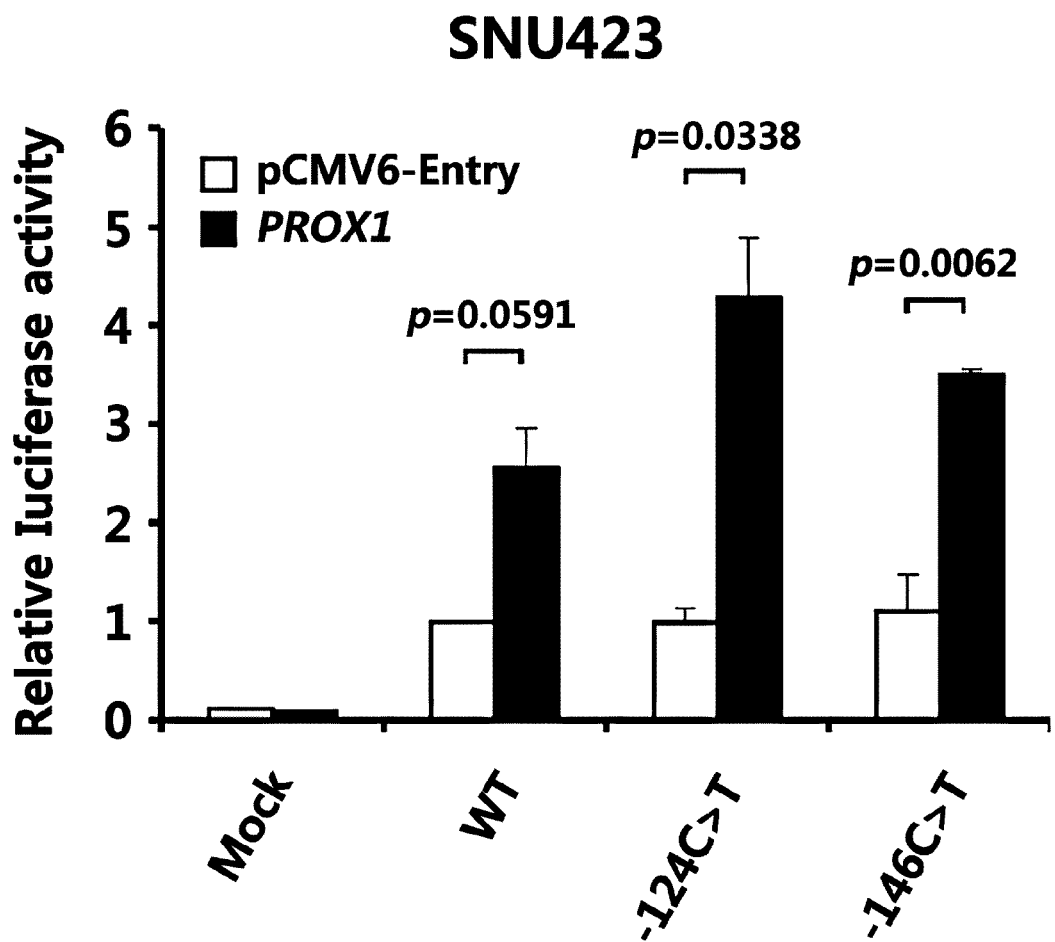

[FIG. 9A]

| Case | -124C>T | -146C>T | rs2853669 | TERT | PROX1 | GABPα | ETS2 | HBx |
|---|---|---|---|---|---|---|---|---|
| HCC 1 | G>A | WT | CC | 12.7 | 433.7 | 149.1 | 2012.0 | full |
| HCC 2 | WT | WT | WT | 29.1 | 260.1 | 143.0 | 1091.5 | ΔC |
| HCC 3 | WT | WT | TC | 646.4 | 261.1 | 119.8 | 2007.3 | ΔC |
| HCC 4 | G>A | WT | CC | 1.9 | 288.4 | 125.6 | 4521.0 | ΔC |
| HCC 5 | WT | WT | TC | 600.0 | 289.6 | 144.5 | 1883.4 | full |
| HCC 6 | G>A | WT | WT | 8.6 | 245.5 | 174.2 | 1526.6 | ΔC |
| HCC 7-1 | G>A | WT | WT | 1.7 | 338.6 | 117.1 | 8038.1 | ΔC |
| HCC 7-2 | WT | WT | WT | 0.8 | 162.3 | 250.4 | 4261.9 | full |
| HCC 8-1 | WT | WT | WT | 1299.9 | 130.7 | 42.1 | 1506.8 | full |
| HCC 8-2 | G>A | WT | WT | 5.5 | 180.8 | 85.7 | 3104.8 | full |
| HCC 9-1 | G>A | WT | WT | 2.1 | 164.1 | 144.0 | 4096.6 | full |
| HCC 9-2 | G>A | WT | WT | | | | | |
| HCC 10 | WT | WT | TC | 8.7 | 419.6 | 195.7 | 1097.6 | ΔC |
| HCC 11 | WT | WT | WT | 70.4 | 87.5 | 88.7 | 830.0 | full |
| HCC 12 | WT | WT | WT | 13.0 | 205.2 | 164.7 | 2293.6 | full |
| HCC 13-1 | WT | WT | TC | 547.1 | 211.4 | 108.3 | 11163.5 | full |
| HCC 13-2 | WT | WT | TC | | | | | |
| HCC 14 | G>A | WT | WT | | | | | |
| HCC 15 | WT | WT | WT | 0.4 | 70.1 | 36.4 | 1959.4 | full |
| HCC 16 | WT | WT | TC | 69.3 | 137.1 | 30.4 | 2151.3 | full |
| HCC 17 | G>A | WT | TC | 0.5 | 66.8 | 53.1 | 2016.6 | ΔC |
| HCC 18 | WT | WT | WT | 15.2 | 118.6 | 36.2 | 3573.8 | full |
| HCC 19 | WT | WT | TC | 121.0 | 116.3 | 80.9 | 1599.9 | full |
| HCC 20 | WT | WT | WT | 0.1 | 161.9 | 40.8 | 2080.8 | ΔC |
| HCC 21 | WT | WT | TC | 0.7 | 459.0 | 271.8 | 1342.8 | full |
| HCC 22 | G>A | WT | WT | 0.0 | 122.6 | 39.1 | 2745.0 | full |
| HCC 23 | WT | WT | WT | 6.0 | 104.5 | 63.8 | 694.6 | full |
| HCC 24 | WT | WT | TC | 8.9 | 199.5 | 31.9 | 708.0 | ΔC |
| HCC 25 | WT | WT | WT | 34.1 | 797.9 | 105.8 | 1423.1 | ΔC |
| HCC 26 | WT | WT | WT | 1.6 | 42.4 | 20.8 | 465.3 | full |
| HCC 27 | G>A | WT | TC | 0.4 | 189.8 | 54.0 | 3210.6 | ΔC |
| HCC 28 | WT | WT | WT | 14.5 | 197.6 | 20.6 | 2549.2 | ΔC |
| HCC 29 | WT | WT | WT | 136.3 | 234.8 | 83.0 | 2349.7 | full |
| HCC 30 | WT | WT | TC | 0.7 | 270.6 | 119.9 | 1627.5 | ΔC |
| HCC 31 | WT | WT | TC | 1.1 | 238.3 | 62.0 | 834.5 | ΔC |
| HCC 32 | WT | WT | CC | 4.2 | 345.9 | 35.0 | 816.1 | full |
| HCC 33 | WT | WT | TC | 0.1 | 253.0 | 57.9 | 815.9 | ΔC |
| HCC 34 | WT | WT | WT | 8.5 | 296.5 | 55.6 | 639.5 | ΔC |
| HCC 35 | WT | WT | TC | 1.5 | 256.3 | 49.6 | 648.4 | ΔC |
| HCC 36 | WT | WT | WT | 1309.1 | 528.1 | 137.4 | 452.7 | full |
| HCC 37 | WT | WT | WT | 1.1 | 111.7 | 24.6 | 647.1 | full |
| HCC 38 | WT | WT | WT | 94.5 | 284.0 | 122.7 | 301.0 | ΔC |
| HCC 39 | WT | WT | WT | 87.6 | 262.7 | 89.8 | 635.9 | full |
| HCC 40 | WT | WT | TC | 0.6 | 275.7 | 63.5 | 1431.3 | ΔC |
| HCC 41 | WT | WT | TC | 0.6 | 227.6 | 50.4 | 161.3 | ΔC |
| HCC 42 | WT | WT | TC | 108.9 | 302.0 | 39.8 | 355.4 | full |
| HCC 43 | WT | WT | TC | 2.2 | 286.2 | 87.2 | 526.8 | full |
| HCC 44 | WT | WT | TC | 0.2 | 651.9 | 160.9 | 723.7 | full |
| HCC 45 | WT | WT | WT | 0.9 | 437.8 | 88.7 | 454.5 | ΔC |
| HCC 46 | WT | WT | TC | 94.5 | 195.1 | 61.2 | 1531.6 | ΔC |
| HCC 47 | G>A | WT | TC | 2.0 | 228.7 | 25.0 | 496.8 | full |

[FIG. 9B]

| Case | -124C>T | -146C>T | rs2853669 | TERT | PROX1 | GABPα | ETS2 | HBx |
|---|---|---|---|---|---|---|---|---|
| HCC 48 | WT | WT | TC | 1.6 | 267.2 | 45.5 | 1154.1 | full |
| HCC 49 | WT | WT | TC | 9.2 | 495.3 | 90.6 | 1184.9 | full |
| HCC 50 | G>A | WT | CC | 2.3 | 240.1 | 119.3 | 681.9 | full |
| HCC 51 | G>A | WT | WT | 3.6 | 252.8 | 58.6 | 293.6 | ΔC |
| HCC 52 | WT | WT | TC | 139.6 | 149.7 | 25.9 | 367.0 | full |
| HCC 53 | WT | WT | TC | 311.4 | 271.9 | 73.2 | 307.0 | ΔC |
| HCC 54 | WT | WT | WT | 15.7 | 467.2 | 62.7 | 256.2 | full |
| HCC 55 | WT | WT | WT | 8.2 | 258.2 | 62.5 | 465.7 | ΔC |
| HCC 56 | WT | WT | TC | 12.1 | 289.2 | 46.2 | 440.3 | ΔC |
| HCC 57 | WT | WT | CC | 6.6 | 260.3 | 42.2 | 581.0 | full |
| HCC 58 | G>A | WT | TC | 3.0 | 277.6 | 43.5 | 488.6 | full |
| HCC 59 | WT | WT | TC | 453.4 | 118.9 | 49.7 | 1068.7 | full |
| HCC 60 | WT | WT | WT | 160.1 | 428.1 | 64.2 | 788.3 | full |
| HCC 61 | G>A | WT | WT | 9.8 | 188.4 | 45.5 | 426.1 | ΔC |
| HCC 62 | G>A | WT | TC | 8.0 | 115.6 | 206.7 | 1150.9 | full |
| HCC 63 | WT | WT | TC | 1.6 | 253.9 | 30.3 | 365.6 | ΔC |
| HCC 64 | G>A | WT | WT | 20.3 | 206.8 | 67.4 | 313.1 | ΔC |
| HCC 65 | WT | WT | WT | 2.5 | 192.4 | 90.3 | 419.4 | ΔC |
| HCC 66 | WT | WT | WT | 3.9 | 163.9 | 18.1 | 92.6 | ΔC |
| HCC 67 | WT | WT | CC | 45.6 | 197.3 | 65.6 | 886.8 | ΔC |
| HCC 68 | WT | WT | TC | 501.0 | 173.9 | 42.7 | 354.4 | ΔC |
| HCC 69 | G>A | WT | WT | 2.7 | 271.0 | 40.1 | 412.3 | ΔC |
| HCC 70 | WT | WT | TC | 617.4 | 166.3 | 57.6 | 611.4 | full |
| HCC 71 | G>A | WT | TC | 7.6 | 169.3 | 46.2 | 472.5 | ΔC |
| HCC 72 | WT | WT | TC | 0.4 | 127.7 | 56.2 | 370.7 | full |
| HCC 73 | G>A | WT | WT | 11.7 | 152.2 | 26.0 | 297.9 | full |
| HCC 74 | WT | WT | CC | 53.2 | 207.0 | 93.7 | 1329.4 | ΔC |
| HCC 75 | WT | WT | TC | 1.3 | 178.8 | 109.5 | 1006.8 | ΔC |
| HCC 76 | WT | WT | CC | 2232.7 | 168.6 | 53.6 | 537.1 | ΔC |
| HCC 77 | WT | WT | WT | 3.5 | 372.7 | 90.8 | 370.4 | ΔC |
| HCC 78 | G>A | WT | CC | 2.6 | 169.5 | 27.1 | 379.6 | full |
| HCC 79 | G>A | WT | WT | 2.7 | 257.5 | 30.7 | 273.9 | ΔC |
| HCC 80 | G>A | WT | TC | 5.5 | 321.1 | 75.8 | 825.7 | full |
| HCC 81 | G>A | WT | TC | 2.7 | 499.3 | 133.7 | 519.4 | ΔC |
| HCC 82 | WT | WT | TC | 10.5 | 504.6 | 117.7 | 888.1 | full |
| HCC 83 | WT | WT | WT | 21.5 | 477.2 | 80.7 | 930.1 | full |
| HCC 84 | WT | WT | TC | 3.3 | 687.7 | 104.4 | 407.0 | ΔC |
| HCC 85 | G>A | WT | WT | 2.1 | 171.2 | 64.6 | 465.4 | full |
| HCC 86 | WT | WT | WT | 6.1 | 274.7 | 36.0 | 235.8 | ΔC |
| HCC 87 | WT | WT | CC | 2401.4 | 232.2 | 102.9 | 346.3 | ΔC |
| HCC 88 | WT | WT | TC | 8.0 | 348.3 | 69.5 | 679.8 | full |
| HCC 89 | G>A | WT | WT | 5.8 | 543.1 | 145.6 | 1203.9 | full |
| HCC 90 | G>A | WT | TC | 4.4 | 207.8 | 67.5 | 727.8 | ΔC |
| HCC 91 | WT | WT | TC | 2.0 | 123.1 | 35.3 | 395.5 | ΔC |
| HCC 92 | WT | WT | TC | 0.3 | 322.4 | 42.8 | 524.9 | full |
| HCC 93 | WT | WT | WT | 53.4 | 348.2 | 118.9 | 428.0 | ΔC |
| HCC 94 | WT | WT | TC | 3.6 | 229.8 | 66.2 | 2111.5 | ΔC |
| HCC 95 | WT | WT | WT | 0.0 | 349.3 | 86.2 | 1063.7 | ΔC |
| HCC 96 | G>A | WT | WT | 4.8 | 173.9 | 18.5 | 161.8 | full |
| HCC 97 | WT | WT | WT | 4.8 | 180.6 | 61.5 | 1008.8 | full |
| HCC 98 | WT | WT | TC | 0.0 | 360.3 | 50.9 | 1518.4 | ΔC |

[FIG. 10]
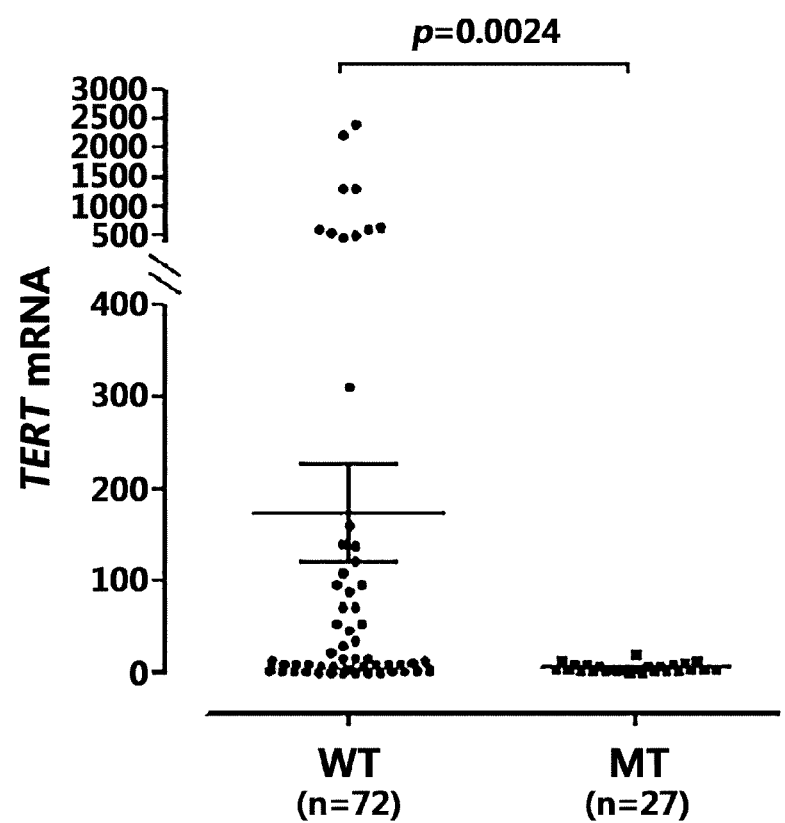

[FIG. 11A]
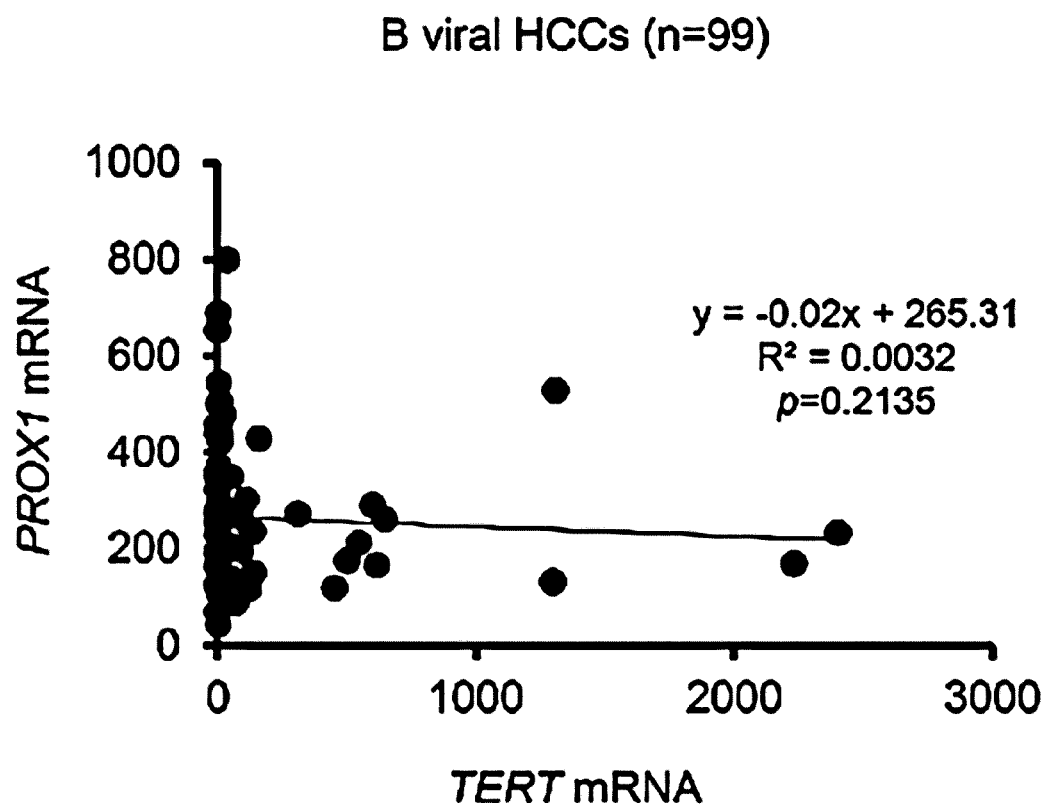

[FIG. 11B]
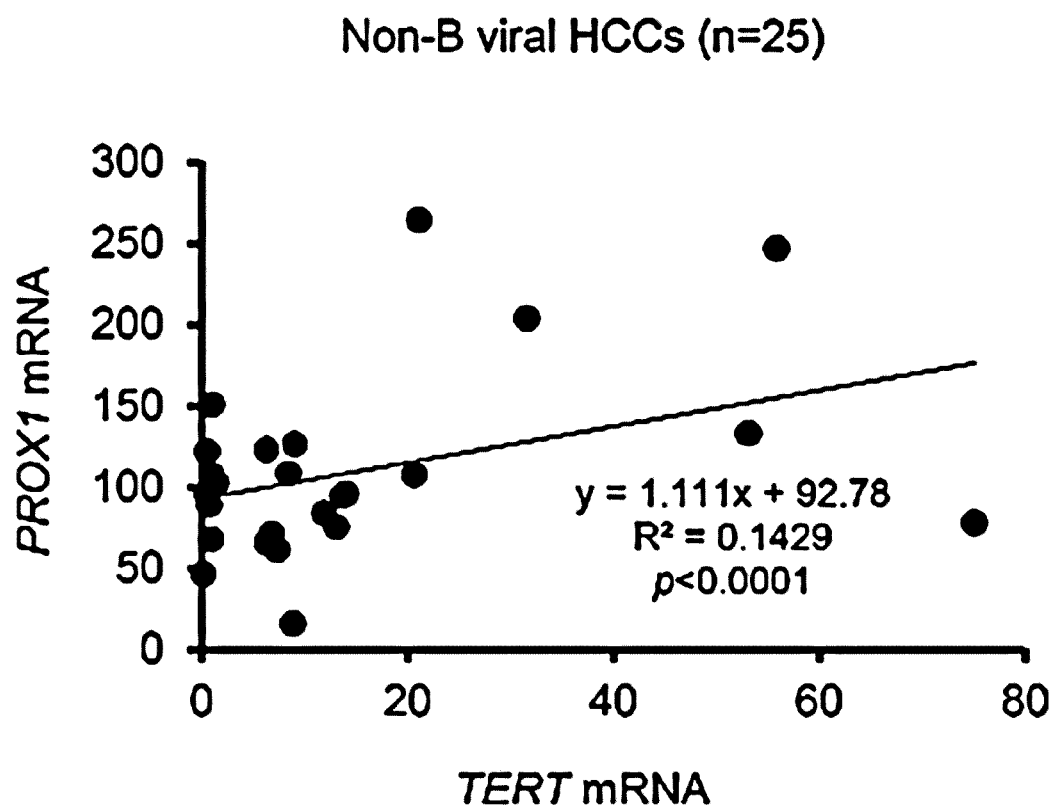

COMPOSITION FOR REGULATING EXPRESSION OF PROX1 OR EXPRESSION OF TELOMERASE REVERSE TRANSCRIPTASE COMPRISING ACTIVITY REGULATOR OR METHOD FOR SCREENING TELOMERASE REVERSE TRANSCRIPTASE REGULATOR

REFERENCE TO SEQUENCE LISTING SUBMITTED VIA EFS-WEB

This application includes an electronically submitted sequence listing in .txt format. The .txt file contains a sequence listing entitled "5398-0130PUS1_ST25.txt" created on Mar. 30, 2023 and is 3,610 bytes in size. The sequence listing contained in this .txt file is part of the specification and is hereby incorporated by reference herein in its entirety.

CROSS REFERENCE TO RELATED APPLICATIONS

This application is the National Phase of PCT/KR2018/012383 filed on Oct. 19, 2018, which claims priority under 35 U.S.C. § 119(a) to Patent Application No. 10-2017-0146274 filed in the Republic of Korea on Nov. 3, 2017, all of which are hereby expressly incorporated by reference into the present application.

TECHNICAL FIELD

In the present specification, based on the correlation between prospero homeobox protein 1 (PROX1) and telomerase reverse transcriptase (TERT), a composition for regulating expression of TERT, a method for screening a TERT expression regulator, a composition for diagnosing a TERT expression status, a diagnostic kit, a method for providing information for diagnosis, or a method for providing information for cancer diagnosis are disclosed.

BACKGROUND ART

A telomere is a special structure found at the end of eukaryotic chromosomes, which prevents degradation or end-to-end fusion of the chromosomes. Telomeric DNA is a primary structure composed of tandem repeats (TTAGGG in humans) whose length varies from hundreds of bp in lower eukaryotic cells to thousands of bp in mammalian cells. The telomeric DNA portion exhibits GC imbalance (GC-rich) as in the centromeric region. This property leads to incomplete replication of the G-strand by the conventional DNA polymerase when the chromosome is replicated, so that the exposed opposite C-strand is degraded by nuclease or the telomeric end portion is completed through synthesis by telomerase.

Telomerase is a ribonucleoprotein complex composed of the active subunit TERT (human telomerase reverse transcriptase) and the component TR (telomerase RNA) which provides a template for synthesis of telomeric DNA. In all telomerase active subunits, the conserved domain is structurally related with the active domain of retroviral and retrotransposon reverse transcriptases (RTs). Although TERT and TR are the basic units of the telomerase ribonucleoprotein, other proteins are also associated structurally or temporarily with this enzyme complex.

Telomerase acts as a reverse transcriptase in telomere extension, and prevents the loss of telomeres caused by the end replication problem. Without telomerase, telomere is shortened after each cycle of cell division, which renders the chromosomes unstable, thereby leading to aging, apoptosis and cell death. Telomerase is inactive in somatic cells but is active in 90% of cancer cells, where the telomerase is activated. Although telomerase activation may be dangerous because telomerase can mimic the onset of cancer, a telomerase enhancer can theoretically be used as an antiaging agent and can be clinically useful for certain medical conditions. In contrast, a telomerase inhibitor may be useful in fighting against cancer. Cancer and aging are closely related to each other. Protective intervention in cancer leads to premature aging, while immortalization of cells is required in the formation of malignant cancer cells. Despite the theoretical risk of activation of carcinogenesis, the activation of telomerase may decrease the rate of aging.

The assessment of telomere length is important in the understanding of biological and clinical significance of the telomere. The telomere length serves as a useful indicator in the study of the chromosomal stability, telomerase activity and/or expression, proliferative capacity and aging process of cells. The clinical value of telomeres can be demonstrated in cancer, premature aging syndrome or segmental progeria; genetic anomalies, diseases resulting from chromosomal instability, such as Bloom syndrome (a rare inherited disorder characterized by a high frequency of breakage and rearrangements in chromosomes), and aging-associated diseases, such as Werner's syndrome (a rare illness occurring in young people, characterized by premature aging). The dynamics of telomere length show distinct patterns in specific disease progressions. Therefore, it can be usefully used in the prognosis of diseases.

The inventors of the present disclosure have studied on the correlation between telomeres and liver cancer. In doing so, they have identified that PROX1 acts as a factor regulating the expression of telomerase reverse transcriptase by binding to the telomerase reverse transcriptase primer and also acts as a factor regulating the expression of telomerase reverse transcriptase in non-hepatitis B virus-associated liver cancer, and have completed the present disclosure.

REFERENCES OF RELATED ART

Patent Documents (Patent document 1) Korean Patent Registration Publication No. 10-1600374.
(Patent document 2) Korean Patent Publication No. 10-2009-0052670.

DESCRIPTION OF GOVERNMENT-SUPPORTED RESEARCH AND DEVELOPMENT

This research was conducted by Yonsei University under the support from the National Research Foundation of Korea of the Ministry of Science, ICT and Future Planning (Bio & Medical Technology Development Program; Screening and verification of co-regulatory factors of cancer and obesity in human liver cancer; Project ID: 1711029890) and the National Research Foundation of Korea of the Ministry of Science and ICT (Bio & Medical Technology Development Program; Construction of clinical-genomic DB for liver cancer and functional-pathological verification of new drug targets; Project ID: 1711057966).

Disclosure

Technical Problem

In an aspect, the present disclosure is directed to providing a composition for regulating expression of TERT or a method for screening a TERT expression regulator.

In an aspect, the present disclosure is also directed to providing a composition for diagnosing a TERT expression status, a diagnostic kit, a method for providing information for diagnosis or a method for providing information for diagnosis of non-hepatitis B virus-associated liver cancer.

Technical Solution

In an aspect, the present disclosure provides a composition for regulating expression of TERT, which contains a PROX1 expression or activity regulator.

In another aspect, the present disclosure provides a method for regulating expression of TERT, which includes a step of administering a PROX1 expression or activity regulator to a subject in need thereof.

In another aspect, the present disclosure provides a use of a PROX1 expression or activity regulator for preparation of a composition for regulating expression of TERT.

In another aspect, the present disclosure provides a PROX1 expression or activity regulator for regulating expression of TERT.

In another aspect, the present disclosure provides a method for screening a TERT expression regulator, which includes: (a) a step of treating isolated cells with a candidate material of a TERT expression regulator; and (b) a step of measuring the expression or activity level of PROX1 in the cells.

In another aspect, the present disclosure provides a composition for diagnosing a TERT expression status, which contains an agent measuring the expression or activity level of PROX1.

In another aspect, the present disclosure provides a use of an agent measuring the expression or activity level of PROX1 for preparation of a composition for diagnosing a TERT expression status or for providing information for the diagnosis.

In another aspect, the present disclosure provides an agent measuring the expression or activity level of PROX1 for diagnosing a TERT expression status or for providing information for the diagnosis.

In another aspect, the present disclosure provides a kit for diagnosing a TERT expression status, which includes the composition.

In another aspect, the present disclosure provides a method for providing information for diagnosis of a TERT expression status, which includes: a step of measuring the expression or activity level of PROX1 from a biological sample; and a step of providing the measured expression or activity level of PROX1 as information for diagnosis of a TERT expression status.

In another aspect, the present disclosure provides a method for providing information for diagnosis of non-hepatitis B virus-associated liver cancer, which includes: a step of measuring the expression or activity level of PROX1 from a biological sample; and a step of providing the measured expression or activity level of PROX1 as information for diagnosis of non-hepatitis B virus-associated liver cancer.

In another aspect, the present disclosure provides a method for providing information for cancer diagnosis, which includes: a step of measuring the expression or activity level of PROX1 from a biological sample; and a step of providing the measured expression or activity level of PROX1 as information for cancer diagnosis, wherein, in the step of providing the information, the measured expression or activity level of PROX1 is provided as information for diagnosis of non-hepatitis B virus-associated liver cancer but hepatitis B virus-associated liver cancer is excluded from diagnosis.

Advantageous Effects

In an aspect, the PROX1 of the present disclosure may bind to a TERT promoter, in particular a mutant TERT promoter in which base substitution occurs at the −124 or −146 bp position to regulate the expression of TERT, and the expression of TERT in non-hepatitis B virus-associated liver cancer can be inhibited specifically among liver cancers. Accordingly, the present disclosure may be utilized in various biomedical fields including compositions for regulating the expression of TERT, compositions for preventing, ameliorating or treating hepatitis B virus-associated liver cancer, and the like.

BRIEF DESCRIPTION OF DRAWINGS

FIGS. 1A-1C show a result of investigating the change in the activity of a TERT promoter in cancer cells depending on genetic variation of the TERT promoter by luciferase assay. Specifically, FIG. 1A shows a result for HepG2 cells, FIG. 1B shows a result for Hep3B cells, and FIG. 1C shows a result for PLC/PRF/5 cells.

FIGS. 2A-2B show a result of screening proteins involved in the transcription of a TERT promoter through oligo pull-down assay in combination with liquid chromatography-tandem mass spectrometry (LC-MS/MS). Specifically, FIG. 2A shows the $R_{sc}$ values of proteins enhanced in a mutant promoter as compared to a wild-type promoter, and FIG. 2B shows an LS-MS/MS spectrum of PROX1.

FIG. 3 shows a result of investigating the binding affinity of PROX1 for a TERT promoter by immunoblot assay.

FIG. 4 shows a result of investigating the change of the binding affinity of PROX1 for a TERT promoter depending on the mutation of an ETS/TCF motif by immunoblot assay.

FIG. 5 shows a result of investigating the change of the binding affinity of endogenous PROX1 depending on cancer cell types by immunoblot assay.

FIG. 6A schematically shows the sequences of amplicons 1-3, and FIG. 6B shows a result of investigating the binding affinity between a TERT promoter and endogenous PROX1 by chromatin immunoprecipitation (ChIP) assay.

FIGS. 7A-7B show a result of investigating the transcriptional regulation of the TERT gene by PROX1 by luciferase assay. Specifically, FIG. 7A shows a result for Hep3B cells, and FIG. 7B shows a result for HepG2 cells.

FIG. 8 shows a result of investigating the transcriptional regulation of the TERT gene by PROX1 by luciferase assay using SNU423 cells.

FIGS. 9A-9B show a result of investigating the clinicopathologic and diagnostic characteristics of TERT promoter mutation for hepatitis B virus-associated liver cancer.

FIG. 10 shows a result of investigating the clinicopathologic and diagnostic characteristics of TERT promoter mutation for hepatitis B virus-associated liver cancer by q-PCR.

FIGS. 11A-11B show a result of investigating the correlation between TERT and PROX1 mRNA expression depending on liver cancer types by qRT-PCR. Specifically, FIG. 11A shows a result for hepatitis B virus-associated liver, and FIG. 11B shows a result for non-hepatitis B virus-associated liver cancer.

BEST MODE

A detailed description is given hereinafter.

In an aspect, the present disclosure provides a composition for regulating expression of TERT, which contains a PROX1 expression or activity regulator.

In the present specification, the 'PROX1' is an acronym for 'prospero homeobox protein 1' and refers to a protein that in humans is encoded by the PROX1 gene. Hereinafter, the term is used to refer to both the gene and the protein.

In the present specification, the 'PROX1 expression or activity regulator' refers to a substance that regulates the expression or activity of PROX1. More specifically, it may include all substances that decrease or increase the expression or activity of PROX1 by decreasing or increasing the expression of PROX1 in transcription level or inhibiting or promoting its activity, by acting on PROX1 directly or indirectly, e.g., by acting on its ligand.

Specifically, the PROX1 expression or activity regulator may be a PROX1 expression or activity inhibitor. In this case, in an exemplary embodiment, the present disclosure may provide a composition for inhibiting expression of TERT, which contains a PROX1 expression or activity inhibitor.

In the present specification, the 'TERT' is an acronym for telomerase reverse transcriptase. It is a catalytic subunit of the enzyme telomerase, which, together with the telomerase RNA component (TERC), comprises the most important unit of the telomerase. According to an exemplary embodiment of the present disclosure, since PROX1 is a transcription factor for TERT, the expression of TERT may be inhibited by inhibiting the expression or activity of PROX1, by inhibiting binding of the transcription factor to a TERT primer. Therefore, a PROX1 expression or activity inhibitor may be used to inhibit the expression of TERT.

The 'PROX1 expression or activity inhibitor' may be a compound, a nucleic acid, a peptide, a virus, or a vector including the nucleic acid, capable of inhibiting the expression or activity of PROX1 by targeting PROX1, although not being limited thereto. For example, it may be a siRNA (small interfering RNA), a shRNA, a miRNA, an antisense oligonucleotide, a ribozyme, a DNAzyme, a PNA (peptide nucleic acid), etc., specifically a siRNA, a shRNA, a miRNA or an antisense oligonucleotide, more specifically a siRNA, that inhibits the expression of PROX1 mRNA by specifically binding to PROX1 mRNA, although not being limited thereto.

The 'siRNA' refers to a nucleic acid molecule capable of mediating RNA interference or gene silencing. It is a small RNA fragment with a size of 21-25 nucleotides. The siRNA of the present disclosure may have a double-stranded structure consisting of a sense strand (a sequence corresponding to an mRNA sequence) and an antisense strand (a sequence complementary to the mRNA sequence), which are located opposite to each other. Furthermore, the siRNA may have a single-stranded structure consisting of self-complementary sense and antisense strands. The double-stranded portion of the siRNA of the present disclosure, in which RNAs pair up, is not limited to a completely paired nucleotide segment, and may include a non-pairing portion due to a mismatch (the corresponding bases are not complementary), a bulge (lacking in the corresponding base on one strand), etc.

The siRNA may have a base sequence represented by SEQ ID NO 1 or SEQ ID NO 2, and a variant of the base sequence represented by SEQ ID NO 1 or SEQ ID NO 2 is also included in the scope of the present disclosure. It includes a functional equivalent of the siRNA represented by SEQ ID NO 1 or SEQ ID NO 2 of the present disclosure, e.g., a variant with a part of the sequence represented by SEQ ID NO 1 or SEQ ID NO 2 modified by deletion, substitution or insertion, which is capable of exhibiting the same function of knocking out the PROX1 gene of the siRNA consisting of the base sequence of SEQ ID NO 1 or SEQ ID NO 2.

Specifically, the siRNA may include a sequence having sequence homology to the base sequence of SEQ ID NO 1 or SEQ ID NO 2 of 70% or higher, more specifically 80% or higher, further more specifically 90% or higher, most specifically 95% or higher. The "sequence homology (%)" to a polynucleotide or an amino acid is identified by comparing a comparison region of two optimally arranged sequences.

The 'PROX1 activity inhibitor' includes, for example, an antibody which inhibits the activity of the PROX1 protein by binding specifically to the PROX1 protein, or an antigen-binding fragment, aptamer, compound, etc. thereof, specifically an antibody, although not being limited thereto.

The antibody refers to a specific protein molecule directed to an antigenic site as a term known in the art. For the purpose of the present disclosure, the antibody refers to an antibody binding specifically to PROX1, and the antibody may be prepared according to a conventional method from a protein encoded by the gene by cloning the gene into an expression vector. It also includes a partial peptide that can be made from the protein. The type of the antibody of the present disclosure is not particularly limited. A polyclonal antibody or a monoclonal antibody may be used and a portion of thereof may also be used as long as it has antigen-binding ability. An immunoglobulin antibody is also included in the antibody of the present disclosure. Furthermore, a special antibody such as a humanized antibody is also included in the antibody of the present disclosure. Specifically, rabbit anti-PROX1 (11067-2-AP, Proteintech, Rosemont, IL, USA) may be used in the present disclosure, although not being limited thereto.

The composition may be provided in various forms.

For example, the present disclosure provides a pharmaceutical composition for regulating expression of TERT, which contains a PROX1 expression or activity regulator. In an exemplary embodiment, the present disclosure may provide a pharmaceutical composition for preventing or treating non-hepatitis B virus-associated liver cancer, wherein the composition contains a PROX1 expression or activity inhibitor.

In the present specification, 'pharmaceutical' refers to the field of studying a substance used to prevent or treat a disease.

In the present specification, 'prevention' means any action of suppressing or delaying the onset of hepatitis C virus-associated liver cancer or alcoholic liver cancer by administering the composition.

In the present specification, 'treatment' means any action of treating hepatitis C virus-associated liver cancer or alcoholic liver cancer by administering the composition.

The composition has a preventive or therapeutic use for non-hepatitis B virus-associated liver cancer, and exhibits preventive or therapeutic for non-hepatitis B virus-associated liver cancer. That is to say, in an exemplary embodiment of the present disclosure, the prevention or treatment sought for through the regulation of the expression or activity of PROX1 is limited to non-hepatitis B virus-associated liver cancer. Based on this, a more effective prevention or treatment of liver cancer can be sought for.

The non-hepatitis B virus-associated liver cancer includes all liver cancers except the liver cancer caused by hepatitis B virus. It may be specifically hepatitis A virus-associated liver cancer, hepatitis C virus-associated liver cancer or alcoholic liver cancer, more specifically hepatitis C virus-associated liver cancer or alcoholic liver cancer, although not being limited thereto.

In the present specification, 'administration' means providing a composition containing a PROX1 expression or activity inhibitor to a subject by any adequate method. The PROX1 expression or activity inhibitor may be administered in a pharmaceutically effective amount.

In the present specification, the 'pharmaceutically effective amount' refers to an amount sufficient to treat a disease, at a reasonable benefit/risk ratio applicable to medical treatment. The effective dosage level may be determined depending on the subject's type, the severity of the disease, the subject's age and sex, the type of the infecting virus, the activity of a drug, the sensitivity to the drug, administration time, administration route, excretion rate, treatment period, drugs used in combination, and other factors well known in the medical field. For example, a daily administration dosage of the PROX1 expression or activity inhibitor may be 0.1-5000 mg/kg/day, more specifically 50-500 mg/kg/day, although not being limited thereto.

The composition may be administered alone or in combination with other therapeutic agents, and may be administered sequentially or simultaneously with conventional therapeutic agents. It can be administered in a single or multiple dosage form. It is important to administer the composition with a minimum amount that can exhibit the maximum effect without causing side effects, in consideration of all the above-described factors, and this amount can be easily determined by those skilled in the art.

The composition may be administered to a subject through various routes. Any mode of administration may be expected. For example, it may be administered orally, rectally, intravenously, intramuscularly or subcutaneously.

The composition may be used alone or in combination with alimentotherapy, physiotherapy or a method using a biological response modifier for prevention or treatment of non-hepatitis B virus-associated liver cancer.

In another exemplary embodiment, the present disclosure provides a functional health food for regulating expression of TERT, which contains a PROX1 expression or activity regulator. In an exemplary embodiment, the present disclosure provides a functional health food composition for preventing or improving non-hepatitis B virus-associated liver cancer, wherein the composition contains a PROX1 expression or activity inhibitor.

In the present specification, the 'functional health food' refers to a food provided with an added value to exert and exhibit the function of the food for a particular purpose by using physical, biochemical or biotechnological techniques or a processed food designed to fully exert a regulatory function related to the regulation of biological defense rhythms, prevention of and recovery from diseases, etc. The functional health food should be unharmful to the body when taken for a long period of time.

The functional health food may contain a sitologically acceptable food supplement additive, and may further contain an adequate carrier, excipient or diluent commonly used in the preparation of functional health foods.

When the functional health food composition is used as a food additive, the composition may be used either alone or in combination with other foods or food ingredients according to a common method. The mixing amount of the active ingredient may be determined adequately depending on the purpose of use (prevention, health improvement or therapeutic treatment). In general, when preparing a food or a drink, the composition of the present disclosure is added in an amount of 15 wt % or less, specifically 10 wt % or less. However, in case of long-term intake for the purpose of health or hygiene improvement, the amount may be less than the above range. Also, the active ingredient may be used in an amount exceeding the above range since it has no safety problem.

The functional health food is not specially limited in type. Examples of the functional health food to which the active ingredient may be added include dairy products including ice creams, various soups, beverages, tea, drinks, alcoholic beverages, multivitamin preparations, etc., and foods provided with added values to exert and exhibit the function of the foods for particular purposes or processed foods designed to fully exert regulatory functions related to the regulation of biological defense rhythms, prevention of and recovery from diseases, etc. are included.

In addition, the functional health food composition disclosed in the present specification may contain various nutrients, vitamins, electrolytes, flavors, colorants, pectic acid and its salts, alginic acid and its salts, organic acids, protective colloidal thickeners, pH control agents, stabilizers, antiseptics, glycerin, alcohols, carbonating agents used in carbonated drinks, etc. In addition, the food composition of the present disclosure may further contain a pulp for preparing natural fruit juice, fruit juice beverages and vegetable beverages. These ingredients may be used independently or in combination. Although the proportion of these additives is of no great importance, it may be generally selected within a range of 0.01-0.1 part by weight based on 100 parts by weight of the composition of the present disclosure.

In another aspect, the present disclosure provides a method for screening a TERT expression regulator, which includes: (a) a step of treating isolated cells with a candidate material of a TERT expression regulator; and (b) a step of measuring the expression or activity level of PROX1 in the cells. In an exemplary embodiment, the TERT expression regulator may be an agent for treating non-hepatitis B virus-associated liver cancer.

The cells of the step (a) may be cells that express or activate PROX1.

The candidate material of the step (a) is a material expected to be capable of inhibiting the expression of TERT or a material expected to be capable of improving the prognosis thereof, and includes a compound, a protein or a natural extract, although not being limited thereto.

Methods for 'measuring the expression level of PROX1' in the step (b) may include polymerase chain reaction (PCR), reverse transcription polymerase chain reaction (RT-PCR), competitive reverse transcription polymerase chain reaction (competitive RT-PCR), real-time reverse transcription polymerase chain reaction (real-time RT-PCR), RNase protection assay (RPA), northern blotting, DNA microarray assay, etc., although not being limited thereto.

Methods for 'measuring the activity level of PROX1' in the step (b) may include western blotting, enzyme-linked immunosorbent assay (ELISA), radioimmunoassay, radio-immunodiffusion, Ouchterlony immunodiffusion, rocket immunoelectrophoresis, Immunohistochemical staining, immunoprecipitation assay, complement fixation assay, flow cytometry (fluorescence-activated cell sorting, FACS), protein chip assay, etc., although not being limited thereto.

The method may further include (c) a step of determining the candidate material as a TERT expression inhibitor if the expression or activity level of PROX1 is decreased by the treatment with the candidate material as compared to cells not treated with the candidate material, and determining the candidate material as a TERT expression promoter if the expression or activity level of PROX1 is increased as compared to cells not treated with the candidate material.

In another aspect, the present disclosure provides a composition for diagnosing a TERT expression status, which contains an agent measuring the expression or activity level of PROX1.

In another aspect, the present disclosure provides a kit for diagnosing a TERT expression status, which includes the composition.

In the present specification, 'diagnosis' refers to detection of the presence or characteristics of a pathological condition. For the purpose of the present disclosure, the diagnosis may be identifying a TERT expression status and, through this, the onset of non-hepatitis B virus-associated liver cancer may be detected. In the present disclosure, determination of the onset of hepatitis B virus-associated liver cancer is excluded.

More specifically, since TERT is a factor indicative of the occurrence of non-hepatitis B virus-associated liver cancer such as hepatitis A virus-associated liver cancer, hepatitis C virus-associated liver cancer and alcoholic liver cancer, diseases caused by chromosomal instability such as premature aging syndrome, segmental progeria, genetic anomalies and Bloom syndrome, aging-associated diseases such as Werner's syndrome, etc., the present disclosure enables diagnosis of the occurrence of cancer, premature aging syndrome, segmental progeria, genetic anomalies, diseases caused by chromosomal instability or aging by diagnosing the TERT expression status of adequately selected cells or tissues.

In addition, the diagnostic kit may include, in addition to the agent measuring the expression or activity level of PROX1, one or more composition, solution or device suitable for analysis, which does not limit the scope of the present disclosure by any means.

For instance, a kit for measuring the expression level of PROX1 may include essential components required to conduct RT-PCR. The RT-PCR kit may further include a test tube or another suitable container, a reaction buffer, a deoxynucleotide (dNTP), an enzyme such as Taq polymerase and reverse transcriptase, a DNase, an RNase inhibitor, DEPC-water, sterile water, etc. in addition to a primer pair specific for a marker gene.

Further, the kit for measuring the expression level of PROX1 may include essential components required to conduct microarray chip assay. The microarray chip kit may include a substrate on which a cDNA for a gene or its fragment is attached as a probe. The substrate may include a cDNA for a quantitative control gene or its fragment and the microarray chip may be prepared easily by using the marker of the present disclosure according to a method commonly used in the art. For example, the marker may be immobilized onto the substrate of the DNA chip as a probe DNA molecule by piezoelectric micropipetting technique, a method of using a pin-type spotter, etc., although not being limited thereto. Specifically, the substrate of the microarray chip may be coated with a functional group selected from a group consisting of aminosilane, poly-L-lysine and aldehyde, although not being limited thereto. In addition, the substrate may be specifically selected from a group consisting of a slide glass, a plastic, a metal, silicon, a nylon membrane and a nitrocellulose membrane, although not being limited thereto.

And, the kit for measuring the activity level of PROX1 may include a substrate for immunological detection of an antibody, an adequate buffer solution, a secondary antibody labeled with a chromogenic enzyme or a fluorescent material, a chromogenic substrate, etc. The substrate may be a nitrocellulose membrane, a 96-well plate made of polyvinyl resin, a 96-well plate made of polystyrene resin, a slide glass, etc., the chromogenic enzyme may be peroxidase, alkaline phosphatase, etc., the fluorescent material may be FITC, RITC, etc., and the chromogenic substrate may be ABTS (2,2'-azino-bis-(3-ethylbenzothiazoline-6-sulfonic acid)), OPD (o-phenylenediamine) or TMB (tetramethylbenzidine).

In another aspect, the present disclosure provides a method for providing information for diagnosis of a TERT expression status by using an agent measuring the expression or activity level of PROX1.

In another aspect, the present disclosure provides a method for providing information for diagnosis of non-hepatitis B virus-associated liver cancer, which includes: a step of measuring the expression or activity level of PROX1 from a biological sample; and a step of providing the measured expression or activity level of PROX1 as information for diagnosis of non-hepatitis B virus-associated liver cancer.

In another aspect, the present disclosure provides a method for providing information for cancer diagnosis, which includes: a step of measuring the expression or activity level of PROX1 from a biological sample; and a step of providing the measured expression or activity level of PROX1 as information for cancer diagnosis, wherein, in the step of providing the information, the measured expression or activity level of PROX1 is provided as information for diagnosis of non-hepatitis B virus-associated liver cancer but hepatitis B virus-associated liver cancer is excluded from diagnosis.

In the present specification, the 'method for providing information for diagnosis' provides objective basic information necessary for diagnosis of a TERT expression status, as a preliminary stage for diagnosis, and the clinical judgment or opinion of a physician is excluded. Furthermore, the method for providing information for diagnosis also includes providing objective basic information necessary for cancer diagnosis, particularly diagnosis of non-hepatitis B virus-associated liver cancer.

In the present specification, the 'biological sample' refers to a sample which is isolated from a subject for measurement of the expression level of a target gene or protein, and includes a tissue, a cell, whole blood, serum, plasma, saliva, sputum, cerebrospinal fluid or urine. For example, the sample of the present disclosure is a sample for diagnosing a TERT expression status from a subject suspected of TERT overexpression, or a sample for diagnosing the onset of non-hepatitis B virus-associated liver cancer from a subject suspected of non-hepatitis B virus-associated liver cancer.

In an exemplary embodiment, the method for providing information for diagnosis of a TERT expression status may further include a step of determining that the expression of TERT has been increased if the expression or activity level of the PROX1 gene is increased as compared to a normal control group. On the contrary, if the expression or activity level of the PROX1 gene is decreased as compared to a normal control group, it may be determined that the expression of TERT has been decreased.

Specifically, since TERT is a factor indicative of the occurrence of non-hepatitis B virus-associated liver cancer such as hepatitis A virus-associated liver cancer, hepatitis C virus-associated liver cancer and alcoholic liver cancer, diseases caused by chromosomal instability such as premature aging syndrome, segmental progeria, genetic anomalies and Bloom syndrome, aging-associated diseases such as Werner's syndrome, etc., the present disclosure may provide information for diagnosis of cancer, premature aging syndrome, segmental progeria, genetic anomalies, diseases caused by chromosomal instability or aging by diagnosing the TERT expression status of adequately selected cells or tissues.

More specifically, in an exemplary embodiment, the method for providing information for diagnosis of non-hepatitis B virus-associated liver cancer of the present disclosure may further include a step of diagnosing as non-hepatitis B virus-associated liver cancer if the expression or activity level of the PROX1 gene is increased as compared to a normal control group. On the contrary, if the expression or activity level of the PROX1 gene is decreased as compared to a normal control group, it may be determined that non-hepatitis B virus-associated liver cancer has not occurred.

In the foregoing description, description of the matter described already above was omitted to avoid unnecessary repetition. And, the terms not defined in the present disclosure have the meanings commonly understood in the technical field to which the present disclosure belongs.

Hereinafter, the present disclosure will be described in detail through examples. However, the following examples are for illustrative purposes only and the scope of the present disclosure is not limited by the examples. The examples are provided to more fully explain the present disclosure to those of ordinary skill in the art.

Example 1. Cell Culturing

HepG2 and Hep3B human liver cancer cells were acquired from American Type Culture Collection (ATCC, Manassas, VA, USA), and SNU423 cells were acquired from Korean Cell Line Bank (Seoul, Korea). The cells were cultured in DMEM (Gibco, Carlsbad, MD, USA) supplemented with 10% fetal bovine serum (Gibco), 100 U/mL penicillin and 10 μg/mL streptomycin at 37° ° C. under the condition of 5% $CO_2$.

Example 2. Investigation of Change in Activation of TERT Promoter Depending on Genetic Variation of TERT Promoter in Cancer Cells by Luciferase Assay The change in the activation of a TERT promoter depending on the genetic variation of the TERT promoter in cancer cells was investigated by luciferase assay. Specifically, 100 ng of a TERT reporter construct including each of a wild-type promoter (WT), a mutant promoter wherein cytosine (C) at −124 bp or −146 bp position from ATG in the TERT gene sequence is substituted with thymine (T) (−124C>T or −146C>T), or a promoter wherein the mutation of the rs2853669 allele is induced (rs-CC), 0.25 ng of a pNL1.1.TK vector (Promega) and 0.5 μL of a FuGENE® HD transfection reagent (Promega) per well were cotransfected into cancer cells, particularly HepG2, Hep3B and PLC/PRF/5 liver cancer cells, in 96-well plates (SPL Life Science, Pocheon, Korea). 48 hours after the transfection, the change in luciferase activity was measured using a Nano-Glo® Dual-Luciferase® reporter assay system (Promega) according to a manual provided by the manufacturer. The luciferase activity was normalized to NanoLuc™ luciferase expression. The result is shown in FIGS. 1A-1C.

The TERT reporter construct was prepared as follows. First, the TERT promoter region (from position −424 to +65 bp from ATG start site) was amplified using DNA extracted from normal liver tissue with rs2853669 TT and CC genotypes, respectively. The amplification was performed by PCR, and each PCR was performed using specific primers containing 5'-extension and SacI and XhoI restriction enzyme sites and Q5® High-Fidelity DNA polymerase (NEB, Ipswich, MA, USA) commonly used in the art. The PCR product was digested with SacI and XhoI, and the prepared amplicons 1-3 were inserted into a pGL3-enhancer vector (Promega, Madison, WI, USA). For high-level transcription of luc+, an SV40 enhancer was located downstream of luc+ and poly(A) signals in the vector.

As shown in FIGS. 1A-1C, the reporter constructs with mutant promoters, especially, the −124C>T promoter, increased TERT promoter activity by about 1.5-2 times as compared to that with the wild-type promoter in all the liver cancer cells. The increase in promoter activity was slightly diminished in the presence of the C allele of rs2853669. In contrast, the allelic variants of rs283669 did not significantly affect the TERT promoter activity in the absence of other promoter mutations. This suggests that the genetic variation in the TERT promoter directly contributes to telomerase activation by increasing the transcription level of TERT which induces the onset of liver cancer.

Example 3. Investigation of Binding Affinity of PROX1 for TERT Promoter 3-1. Screening of Proteins Involved in Transcription of TERT Promoter by Liquid Chromatography-Tandem Mass Spectrometry (LC-MS/MS) Combined with Oligo Pull-Down Assay It is known that a consensus ETS/TCF binding site (CCGGAA) represented by SEQ ID NO 3 induces mutation of the TERT promoter and that TERT transcription is increased by the ETS/TCF transcription factor. Nevertheless, it has not been demonstrated experimentally yet what kind of proteins (i.e., ETS/TCF family proteins or other proteins) directly bind to the de novo sites. Therefore, the proteins involved in the transcription of mutant TERT promoters were detected by liquid chromatography-tandem mass spectrometry (LC-MS/MS) combined with oligo pull-down assay.

Specifically, wild-type WT #1 and mutant 124C>T and 146C>T sequences were synthesized as biotinylated double-stranded oligonucleotides complementary to the TERT promoter (Table 1). Equal volumes of both oligos were resuspened in an annealing buffer (10 mM Tris-HCL [PH 7.4], 50 mM NaCl, 1 mM EDTA), heated for 5 minutes at 95° C. and then annealed by slowly cooling to room temperature. Then, 100 μmol of the annealed oligos were incubated with streptavidin-coated magnetic beads (Dynabead M-280 streptavidin, Invitrogen, Carlsbad, CA, USA) at room temperature for 30 minutes.

TABLE 1

| | SEQ ID NO | Sequence |
|---|---|---|
| WT #1 | 4 | GACCCCTCCCGGGTCCCCGGCCCA GCCCCCTCCGGGCCCTC |
| -124 C > T | 5 | GACCCCTCCCGGGTCCCCGGCCCA GCCCCTTCCGGGCCCTC |
| -146 C > T | 6 | GACCCCTTCCGGGTCCCCGGCCCA GCCCCCTCCGGGCCCTC |

TABLE 2

| | SEQ ID NO | Sequence |
|---|---|---|
| WT #1 | 4 | GACCCCTCCCGGGTCCCCGGCCCAGCCC CCTCCGGGCCCTC |
| WT #2 | 7 | AGCCCCCTCCGGGCCCTC |
| WT #3 | 8 | GACCCCTCCCGGGTCCCC |
| MT | 9 | GACCCTCCGCGCGTCCCCGGCCCAGCCC CCGTCGCGCCCTC |

Separately from this, a nuclear extract was isolated from Hep3B cancer cells with high −124C>T or −146C>T promoter activity. 1 mg of the isolated nuclear extract was added to the magnetic beads and then incubated at 4° C. for 2 hours. For the proteins isolated from the magnetic beads as a result of the incubation, protein-DNA affinity was analyzed by comparing the spectrum count levels of each sample by SDS-PAGE and LS-MS/MS (liquid chromatography-tandem mass spectrometry) generally used in the art. The result is shown in FIG. 2A as the $R_{sc}$ (fold-change ratio) values of the proteins with enhanced mutant promoters as compared to the wild-type promoter. In addition, the LS-MS/MS spectrum of PROX1 is shown in FIG. 2B.

As seen from FIGS. 2A-2B, some proteins were found to have higher binding affinity for oligos with −124C>T and −146C>T substitution than the WT #1 oligo. Among the proteins, PROX1 (prospero homeobox protein 1, molecular weight=83 kDa) which exhibited significant binding affinity, was selected.

3-2. Investigation of Binding Affinity of PROX1 for TERT Promoter by Immunoblot Assay The binding affinity of PROX1 to the TERT promoter, particularly the binding affinity between PROX1 and the TERT promoter for each of the samples WT #1, −124C>T and −146C>T, was validated by immunoblot assay using the samples obtained in Example 3-1 through oligo pull-down assay. The immunoblot assay was conducted using rabbit anti-PROX1 (11067-2-AP, Proteintech, Rosemont, IL, USA) as a primary antibody. The result is shown in FIG. 3.

As seen from FIG. 3, all of the TERT promoters treated with WT #1 oligo or −124C>T and −146C>T oligos showed positive response to PROX1. Although the binding to PROX1 was detected also for WT #1 olig, the affinity was lower than when treated with −124C>T or −146C>T oligo. This means that PROX1 exhibits better binding affinity to the mutant TERT promoter than to the wild-type TERT promoter, and induces better increase in the expression of TERT in cells with mutant TERT promoters.

3-3. Investigation of Change in Binding Affinity of PROX1 for TERT Promoter Depending on Mutation of ETS/TCF Motif by Immunoblot Assay The binding affinity of PROX1 for the TERT promoter, i.e., whether the binding of PROX1 occurs specifically at the ETS/TCF motif represented by SEQ ID NO 3, which is a hot spot in the TERT promoter, was investigated by oligo pull-down assay and immunoblot assay using various wild-type (WT) oligos WT #1, WT #2 and WT #3 and a mutant (MT) oligo with the ETS/TCF motif completely destroyed.

Specifically, oligo pull-down assay and immunoblot assay were conducted in the same manner as described in Examples 3-1 and 3-2, except for using the wild-type (WT) oligos WT #1, WT #2 and WT #3 and the MT oligo described in Table 2. The result is shown in FIG. 4.

As shown in FIG. 4, it was confirmed that PROX1 binds specifically to the wild-type TERT promoter sequences CCGGAG and CCGGGA, and the binding to the MT oligo with the ETS/TCF binding motif completely destroyed was decreased remarkably. This suggests that the binding affinity between the TERT promoter and PROX1 is directly proportional to the scope of the region bound to the ETS/TCF motif in the TERT promoter.

Example 4. Investigation of Binding Affinity of Endogenous PROX1 for TERT Promoter 4-1. Investigation of Binding Affinity of Endogenous PROX1 Depending on Cancer Cell Types by Immunoblot Assay The change in the binding affinity of endogenous PROX1 depending on cell types was investigated by immunoblot assay. The immunoblot assay was conducted by a method generally used in the art by using rabbit anti-PROX1 (11067-2-AP, Proteintech, Rosemont, IL, USA), rabbit anti-COX IV (48844, CST) and rabbit anti-Lamin B1 (ab16048, Abcam) as primary antibodies. The result is shown in FIG. 5. Lamin B1 was used as a nuclear protein marker, and COX IV was used as a cytosolic protein marker.

As seen from FIG. 5, the endogenous PROX1 was detected with a larger quantity in the nucleus (N) than in the cytoplasm (C) of the Hep3B and HepG2 liver cancer cells. But, the endogenous PROX1 was not detected in the SNU423 cells. In addition, the expression level of PROX1 was higher in the Hep3B cells than other cells. This suggests that the activation of the TERT promoter in cancer cells is dependent on the expression pattern of PROX1.

4-2. Investigation of Binding Affinity Between TERT Promoter and Endogenous PROX1 by Chromatin Immunoprecipitation (ChIP) Assay It was investigated whether the endogenous PROX1 in cells binds physically to the TERT promoter by chromatin immunoprecipitation assay. Specifically, chromatin immunoprecipitation assay was carried out on Hep3B cells having the wild-type TERT promoter and HepG2 cells having the −124C>T TERT promoter using the SimpleChIP® Plus enzymatic chromatin IP kit (CST) according to a manual provided by the manufacturer. For this, 5-10 µg of chromatin and 1 µg of PROX1 antibody (11067-2-AP, Proteintech) were used. Subsequently, quantitative real-time PCR (qRT-PCR) was conducted using the primers described in Table 3 in order to quantify the experimental result. The sequences of amplicons 1-3 are shown in FIG. 6A. Amplicons 1 and 2 are replication products of the TERT promoter region including hot spots, and amplicon 3 is a replication product of the 3'-UTR of TERT. The result is shown in FIG. 6B.

TABLE 3

| Name | | SEQ ID NO | Sequence | Annealing temperature (° C.) |
|---|---|---|---|---|
| TERT amplicon 1 | Forward | 10 | CTGCCCCTTCACCTTCCAG | 58 |
| | Reverse | 11 | AGCGCTGCCTGAAACTCG | |
| TERT amplicon 2 | Forward | 12 | CTCCCAGTGGATTCGCGG | 60 |
| | Reverse | 13 | CTGCCTGAAACTCGCGCC | |
| TERT amplicon 3 | Forward | 14 | ATTCGCCATTGTTCACCCCT | 60 |
| | Reverse | 15 | CTGTGTACAGGGCACACCTT | |

As shown in FIGS. 6A-6B, both the amplicons 1 and 2, which are the sequences located between −48 and −286 bp in the promoter were bound to PROX1, but the amplicon 3, which is the sequence located at the 3'-UTR of TERT, was not bound to PROX1, for both cell types. This means that PROX1 binds to the TERT promoter, especially at the hot spots.

Example 5. Investigation of Role of Endogenous PROX1 as Transcription Factor for TERT Gene 5-1. Investigation of Role Transcriptional Regulation of TERT Gene by PROX1 by Luciferase Assay The transcriptional regulation of the TERT gene by PROX1 in Hep3B and HepG2 cells was investigated by conducting qRT-PCR. Specifically, 100 ng of a TERT reporter construct including a wild-type promoter (WT) or a mutant promoter wherein cytosine (C) at 124 bp or 146 bp position is substituted with thymine (T) (−124C>T or −146C>T), 0.25 ng of a pNL1.1.TK vector (Promega), PROX1 siRNAs represented by SEQ ID NOS 1 and 2, and 0.4 μL of a DharmaFECT™ Duo transfection reagent (GE Healthcare, Little Chalfont, UL) per well were cotransfected into cancer cells, particularly HepG2 and Hep3B liver cancer cells, in 96-well plates (SPL Life Science, Pocheon, Korea). Luciferase assay was conducted 48 hours after the transfection. Each step was performed according to the method described in Example 2. The experimental result for the PROX1 siRNA of SEQ ID NO 2 is shown in FIGS. 7A-7B.

SEQ ID NO 1: CCUAUAACUUGUUAUCAUU
(Thermo Fisher Scientific assay ID; n331082)
SEQ ID NO 2: GCUGUAGUGUAUUCACCUA
(Thermo Fisher Scientific assay ID; n331083)

As shown in FIGS. 7A-7B, it was confirmed that the expression of TERT mRNA was remarkably inhibited in the Hep3B and HepG2 cells by PROX1 knockdown. In particular, it was confirmed that the PROX1 knockdown remarkably inhibits not only the activity of the wild-type promoter but also the promoter activity of the −124C>T and −146C>T mutant constructs.

5-2. Investigation of Transcriptional Regulation of TERT Gene by PROX1 by Luciferase Assay Using SNU423 Cells The transcriptional regulation of the TERT gene by PROX1 was investigated more clearly using SNU423 cells not affected by PROX1. Specifically, 50 ng of a TERT reporter construct including a wild-type promoter (WT) or a mutant promoter wherein cytosine (C) at 124 bp or 146 bp position is substituted with thymine (T) (−124C>T or −146C>T), 0.125 ng of a pNL1.1.TK vector (Promega), a pCMV6-PROX1 vector (RC201140, Origene, Beijing, China) and 0.5 μL of a FuGENE® HD transfection reagent (Promega) per well were cotransfected into SNU423 cells, in 96-well plates (SPL Life Science, Pocheon, Korea). Luciferase assay was conducted 48 hours after the transfection. Each step was performed according to the method described in Example 2. The experimental result is shown in FIG. 8.

As shown in FIG. 8, it was confirmed that PROX1 overexpression resulted in about 2.4-fold increase of the activity of wild-type promoter (WT). The activity of the −124C>T and −146C>T promoters was increased by about 4.3- and 3.5-fold, respectively. This suggests that PROX1 is an important transcription factor in the expression of the TERT gene and acts by preferentially binding to the mutant TERT promoter.

Example 6. Investigation of Clinicopathologic and Diagnostic Characteristics of TERT Promoter Mutation 6-1. Investigation of Clinicopathologic and Diagnostic Characteristics of TERT Promoter Mutation for Hepatitis B Virus-Associated Liver Cancer 102 cases of hepatitis B virus-associated liver cancer from 98 patients were investigated. The somatic mutation of rs2853669 in the TERT promoter region was investigated by conducting Sanger sequencing. The result is shown in FIGS. 9A-9B. In addition, the correlation between the genetic variations in the TERT and TERT promoter expression was investigated by qRT-PCR for 99 cases of hepatitis B virus-associated liver cancer. The result is shown in FIG. 10. The analysis was performed in the same manner as in Example 4-1 except that samples from the 102 cases of hepatitis B virus-associated liver cancer were used.

As shown in FIGS. 9A-9B, the incidence of TERT promoter mutation with −124C>T substitution was found in 29 cases (28.4%) of liver cancer, and −146C>T substitution was not found in any cancer. TERT promoter mutation was not found in 5 cases of normal liver and 33 cases of liver cirrhosis. In addition, the variation of rs2853669 was detected in 55 patients (56.1%; TC heterozygotes: 45.9%, CC homozygotes: 10.2%), similar to those in the 1000 genome database of Asian population (52.4%, data available for 285 individuals). This means that the rs2853669 status does not significantly affect the frequency of TERT promoter mutation in patients with hepatitis B virus-associated liver cancer.

Also, as shown in FIG. 10, it was confirmed that the TERT mRNA expression level was remarkably decreased in liver cancer patients with mutant TERT promoters as compared to those with wild-type TERT promoters (p=0.0024). Meanwhile, the TERT mRNA level in liver cancer showed no significant difference depending on the existence of C allele of rs2853669 (SNP). This is contrary to the results of Examples 1-4, suggesting that the PROX1 of the present disclosure is effective only for liver cancers other than the hepatitis B virus-associated liver cancer caused by the HBV gene.

6-2. Investigation of Correlation Between TERT and PROX1 mRNA Expression Depending on Liver Cancer Types by qRT-PCR Analysis It was investigated whether the increased expression of TERT as a transcription factor of a TERT promoter by PROX1 has an effect on liver cancer types other than hepatitis B virus-associated liver cancer by qRT-PCR analysis. Specifically, quantitative real-time PCR (qRT-PCR) was conducted for non-hepatitis B virus-associated liver cancer (14 cases of hepatitis C virus-associated liver cancer and 11 cases of alcoholic liver cancer) using the primers described in Table 3. The result is shown in FIGS. 11A-11B.

As seen from FIG. 11A, no significant correlation was observed between TERT and PROX1 mRNA expression for hepatitis B virus-associated liver cancer. This is consistent with the result of Example 6-1. In contrast, correlation was observed between TERT and PROX1 mRNA expression for non-hepatitis B virus-associated liver cancer, as shown in FIG. 11B. This is consistent with the results of Examples 3-5. These results mean that PROX1 has an effect of specifically regulating expression of TERT in non-hepatitis B virus-associated liver cancer such as hepatitis C virus-associated liver cancer and alcoholic liver cancer.

In summary, the PROX1 of the present disclosure can regulate the expression of TERT by binding to a TERT promoter, particularly to a mutant TERT promoter with base substitution at −124 or −146 bp position, and can specifically inhibit the expression of TERT in non-hepatitis B virus-associated liver cancer. Accordingly, the present disclosure can be utilized in various biomedical fields including compositions for regulating the expression of TERT, compositions for preventing, ameliorating or treating hepatitis B virus-associated liver cancer, and the like.

Hereinafter, the present disclosure will be described in detail through formulation examples. However, the following formulation examples are for illustrative purposes only and the scope of the present disclosure is not limited by the examples.

Formulation Example 1. Preparation of Pharmaceutical Formulations 1-1. Preparation of Powder A powder was prepared by filling a mixture of 20 mg of a PROX1 expression or activity regulator, 100 mg of lactose and 10 mg of talc in a sealed pouch.

1-2. Preparation of Tablet

A tablet was prepared according to a common method after mixing 10 mg of a PROX1 expression or activity regulator, 100 mg of corn starch, 100 mg of lactose and 2 mg of magnesium stearate.

1-3. Preparation of Capsule

A capsule was prepared according to a common method by mixing 10 mg of a PROX1 expression or activity regulator, 3 mg of crystalline cellulose, 14.8 mg of lactose and 0.2 mg of magnesium stearate and filling the mixture in a gelatin capsule.

1-4. Preparation of Injection

An injection was prepared according to a common method by mixing 10 mg of a PROX1 expression or activity regulator, 180 mg of mannitol, 2,974 mg of sterile distilled water for injection and 26 mg of $Na_2HPO_4 \cdot 2H_2O$ per ampoule (2 mL).

1-5. Preparation of Liquid Formulation

According to a common method, after dissolving 20 mg of a PROX1 expression or activity regulator, 10 g of isomerized sugar and 5 g of mannitol in purified water and adding an adequate amount of lemon flavor, the ingredients were mixed. After making the final volume 100 mL by further adding purified water, the resulting liquid formulation was filled in a brown bottle.

Formulation Example 2. Preparation of Food Formulation 2-1. Preparation of Health Food A health food was prepared according to a common method by mixing 100 mg of a PROX1 expression or activity regulator, an adequate amount of a vitamin mixture (70 g of vitamin A acetate, 1.0 mg of vitamin E, 0.13 mg of vitamin $B_1$, 0.15 mg of vitamin $B_2$, 0.5 mg of vitamin $B_6$, 0.2 g of vitamin $B_{12}$, 10 mg of vitamin C, 10 g of biotin, 1.7 mg of nicotinamide, 50 g of folic acid, 0.5 mg of calcium pantothenate), and an adequate amount of a mineral mixture (1.75 mg of ferrous sulfate, 0.82 mg of zinc oxide, 25.3 mg of magnesium carbonate, 15 mg of monopotassium phosphate, 55 mg of dicalcium phosphate, 90 mg of potassium citrate, 100 mg of calcium carbonate, 24.8 mg of magnesium chloride) and preparing the mixture into a granule. The above-described compositions of the vitamin and mineral mixtures are given as relatively preferred examples for health food but may be varied as desired.

2-2. Preparation of Health Drink

According to a common health drink preparation method, 100 mg of a PROX1 expression or activity regulator, 15 g of vitamin C, 100 g of vitamin E (powdered), 19.75 g of iron lactate, 3.5 g of zinc oxide, 3.5 g of nicotinamide, 0.2 g of vitamin A, 0.25 g of vitamin B1, 0.3 g of vitamin B2, and a suitable amount of water were mixed. The resulting solution was heated with agitation at 85° C. for about 1 hour and then filtered. The filtered solution was filled in a sterilized 2-L vessel and then stored in a refrigerator after sealing and sterilization. The above-described composition illustrates a preferable example relatively suitable for a health drink. However, it can be modified as desired according to regional and ethnic preferences such as particular consumers, countries, purpose of use, etc.

The invention claimed is:

1. A method for regulating expression of telomerase reverse transcriptase (TERT), comprising administering a composition comprising a prospero homeobox protein 1 (PROX1) expression or activity regulator to a subject in need thereof;
    wherein the PROX1 expression or activity regulator is a siRNA represented by SEQ. ID. NO.: 1, SEQ. ID. NO.: 2, a sequence having 70% or higher homology to SEQ. ID. NO.: 1, or a sequence having 70% or higher homology to SEQ. ID. NO.: 2.

2. The method for regulating expression of TERT according to claim 1, wherein the PROX1 expression or activity regulator is a PROX1 expression or activity inhibitor.

3. The method for regulating expression of TERT according to claim 1, wherein the PROX1 expression or activity regulator is the siRNA represented by SEQ. ID. NO.: 1, SEQ. ID. NO.: 2, a sequence having 80% or higher homology to SEQ. ID. NO.: 1, or a sequence having 80% or higher homology to SEQ. ID. NO.: 2.

4. The method for regulating expression of TERT according to claim 1, wherein the siRNA is represented by SEQ. ID. NO.: 1 or SEQ. ID. NO.: 2.

5. The method for regulating expression of TERT according to claim 1, wherein the composition is a pharmaceutical composition,
    wherein the composition is for preventing or treating non-hepatitis B virus-associated liver cancer.

6. The method for regulating expression of TERT according to claim 5, wherein the non-hepatitis B virus-associated liver cancer is one or more selected from a group consisting of hepatitis A virus-associated liver cancer, hepatitis C virus-associated liver cancer and alcoholic liver cancer.

7. The method for regulating expression of TERT according to claim 1, wherein the PROX1 expression or activity regulator is the siRNA represented by SEQ. ID. NO.: 1, SEQ. ID. NO.: 2, a sequence having 90% or higher homology to SEQ. ID. NO.: 1, or a sequence having 90% or higher homology to SEQ. ID. NO.: 2.

* * * * *

SEQUENCE LISTING

```
<160> NUMBER OF SEQ ID NOS: 15

<210> SEQ ID NO 1
<211> LENGTH: 19
<212> TYPE: RNA
<213> ORGANISM: Artificial Sequence
<220> FEATURE:
<223> OTHER INFORMATION: PROX1 siRNA

<400> SEQUENCE: 1
ccuauaacuu guuaucauu                                               19

<210> SEQ ID NO 2
<211> LENGTH: 19
```

```
<212> TYPE: RNA
<213> ORGANISM: Artificial Sequence
<220> FEATURE:
<223> OTHER INFORMATION: PROX1 siRNA

<400> SEQUENCE: 2
gcuguagugu auucaccua                                                    19

<210> SEQ ID NO 3
<211> LENGTH: 6
<212> TYPE: DNA
<213> ORGANISM: Artificial Sequence
<220> FEATURE:
<223> OTHER INFORMATION: consensus ETS/TCF binding site

<400> SEQUENCE: 3 ccggaa                                                                   6

<210> SEQ ID NO 4
<211> LENGTH: 41
<212> TYPE: DNA
<213> ORGANISM: Artificial Sequence
<220> FEATURE:
<223> OTHER INFORMATION: wild-type(WT#1) oligo for TERT promoter

<400> SEQUENCE: 4
gacccctccc gggtccccgg cccagccccc tcgggccct c                             41

<210> SEQ ID NO 5
<211> LENGTH: 41
<212> TYPE: DNA
<213> ORGANISM: Artificial Sequence
<220> FEATURE:
<223> OTHER INFORMATION: -124 C>T oligo for TERT promoter

<400> SEQUENCE: 5
gacccctccc gggtccccgg cccagcccct tcgggccct c                             41

<210> SEQ ID NO 6
<211> LENGTH: 41
<212> TYPE: DNA
<213> ORGANISM: Artificial Sequence
<220> FEATURE:
<223> OTHER INFORMATION: -126 C>T oligo for TERT promoter

<400> SEQUENCE: 6
gacccctccc gggtccccgg cccagccccc tcgggccct c                             41

<210> SEQ ID NO 7
<211> LENGTH: 18
<212> TYPE: DNA
<213> ORGANISM: Artificial Sequence
<220> FEATURE:
<223> OTHER INFORMATION: wild-type(WT#2) oligo for TERT promoter

<400> SEQUENCE: 7
agccccctcc gggccctc                                                     18

<210> SEQ ID NO 8
<211> LENGTH: 18
<212> TYPE: DNA
<213> ORGANISM: Artificial Sequence
<220> FEATURE:
<223> OTHER INFORMATION: wild-type(WT#3) oligo for TERT promoter

<400> SEQUENCE: 8
```

-continued gaccoctccc gggtcccc                                                    18

<210> SEQ ID NO 9
<211> LENGTH: 41
<212> TYPE: DNA
<213> ORGANISM: Artificial Sequence
<220> FEATURE:
<223> OTHER INFORMATION: mutant(MT) oligo for TERT promoter

<400> SEQUENCE: 9
gaccctccgc gcgtccccgg cccagccccc gtcgcgccct c                          41

<210> SEQ ID NO 10
<211> LENGTH: 19
<212> TYPE: DNA
<213> ORGANISM: Artificial Sequence
<220> FEATURE:
<223> OTHER INFORMATION: TERT amplicon 1_Forward

<400> SEQUENCE: 10
ctgccccttc accttccag                                                   19

<210> SEQ ID NO 11
<211> LENGTH: 18
<212> TYPE: DNA
<213> ORGANISM: Artificial Sequence
<220> FEATURE:
<223> OTHER INFORMATION: TERT amplicon 1_Reverse

<400> SEQUENCE: 11
agcgctgcct gaaactcg                                                    18

<210> SEQ ID NO 12
<211> LENGTH: 18
<212> TYPE: DNA
<213> ORGANISM: Artificial Sequence
<220> FEATURE:
<223> OTHER INFORMATION: TERT amplicon 2_Forward

<400> SEQUENCE: 12
ctcccagtgg attcgcgg                                                    18

<210> SEQ ID NO 13
<211> LENGTH: 18
<212> TYPE: DNA
<213> ORGANISM: Artificial Sequence
<220> FEATURE:
<223> OTHER INFORMATION: TERT amplicon 2_Reverse

<400> SEQUENCE: 13
ctgcctgaaa ctcgcgcc                                                    18

<210> SEQ ID NO 14
<211> LENGTH: 20
<212> TYPE: DNA
<213> ORGANISM: Artificial Sequence
<220> FEATURE:
<223> OTHER INFORMATION: TERT amplicon 3_Forward

<400> SEQUENCE: 14
attcgccatt gttcacccct                                                  20

<210> SEQ ID NO 15
<211> LENGTH: 20
<212> TYPE: DNA
<213> ORGANISM: Artificial Sequence

```
<220> FEATURE:
<223> OTHER INFORMATION: TERT amplicon 3_Reverse

<400> SEQUENCE: 15
ctgtgtacag ggcacacctt                                              20
```